(12) United States Patent
Devary

(10) Patent No.: US 12,071,488 B2
(45) Date of Patent: Aug. 27, 2024

(54) METHOD OF SENSITIZING CANCER CELLS TO ANTI-CANCER TREATMENT

(71) Applicant: TWO TO BIOTECH LTD., Jerusalem (IL)

(72) Inventor: Yoram Devary, Jerusalem (IL)

(73) Assignee: TWO TO BIOTECH LTD., Jerusalem (IL)

( * ) Notice: Subject to any disclaimer, the term of this patent is extended or adjusted under 35 U.S.C. 154(b) by 0 days.

(21) Appl. No.: 16/613,615

(22) PCT Filed: May 17, 2018

(86) PCT No.: PCT/IL2018/050542
§ 371 (c)(1),
(2) Date: Nov. 14, 2019

(87) PCT Pub. No.: WO2018/211514
PCT Pub. Date: Nov. 22, 2018

(65) Prior Publication Data
US 2020/0115413 A1    Apr. 16, 2020

Related U.S. Application Data

(60) Provisional application No. 62/507,939, filed on May 18, 2017.

(51) Int. Cl.
C07K 7/08      (2006.01)
A61K 38/00     (2006.01)
A61K 45/06     (2006.01)
A61P 35/00     (2006.01)

(52) U.S. Cl.
CPC ............ *C07K 7/08* (2013.01); *A61P 35/00* (2018.01); *A61K 38/00* (2013.01); *A61K 45/06* (2013.01)

(58) Field of Classification Search
None
See application file for complete search history.

(56) References Cited

FOREIGN PATENT DOCUMENTS

| WO | WO 2009/083968  | * | 12/2005 |
| WO |    2009/083968 A1 |   | 7/2009  |
| WO | WO 2005/117887  | * | 7/2009  |
| WO | WO 2012/001674  | * | 1/2012  |
| WO |    2012/038957 A1 |   | 3/2012  |

OTHER PUBLICATIONS

Trebunova et al. (Anticancer Research 32: 2849-2854) (Year: 2012).*
Vyas et al. (J Clin Med Res. 2016;8(2):162-167) (Year: 2016).*
Hong et al. (Breast Cancer Res Treat. Jun. 2013 ; 139(2): 477-488) (Year: 2013).*
Nagai et al. (Cell Reports, 12, 2049-2059, 2015) (Year: 2015).*
Sacchi et al. (Cancer Research 64, 7150-7155, Oct. 1, 2004) (Year: 2004).*
Lu et al. (PLoS ONE 9(11): e113783, 2014) (Year: 2014).*
Fekete et al. (BMC Cancer 2005, 5:114) (Year: 2005).*
Thomas et al. (Cancer Res. Nov. 15, 2004;64(22):8357-64) (Year: 2004).*
Hussner et al. (Mol Pharmacol. May 2012;81(5):679-88) (Year: 2012).*
Andre et al., "Optimal strategies for the treatment of metastatic triple-negative breast cancer with currently approved agents", Annals of Oncology, 2012, vol. 23, (Supplement 6): vi46-vi51.
Sandler et al., "A Novel Human Cytotoxic Cell Activation Factor with anti-Cancer Activity", Recent Advances in Clinical Medicine, 2010, pp. 168-173, ISSN: 1790-5125, ISBN: 978-960-474-165-6.
Yao et al., "Triple-negative breast cancer: is there a treatment on the horizon", Oncotarget, 2017, vol. 8, (No. 1), pp. 1913-1924, DOI: 10.18632/oncotarget.12284.

* cited by examiner

*Primary Examiner* — Sergio Coffa
(74) *Attorney, Agent, or Firm* — BROWDY AND NEIMARK, PLLC

(57) ABSTRACT

A combinational therapy for treatment of cancer. Compositions, methods and kits for treatment of cancer and for sensitizing cancer cells to a broad spectrum of anti-cancer agents.

4 Claims, 14 Drawing Sheets

Specification includes a Sequence Listing.

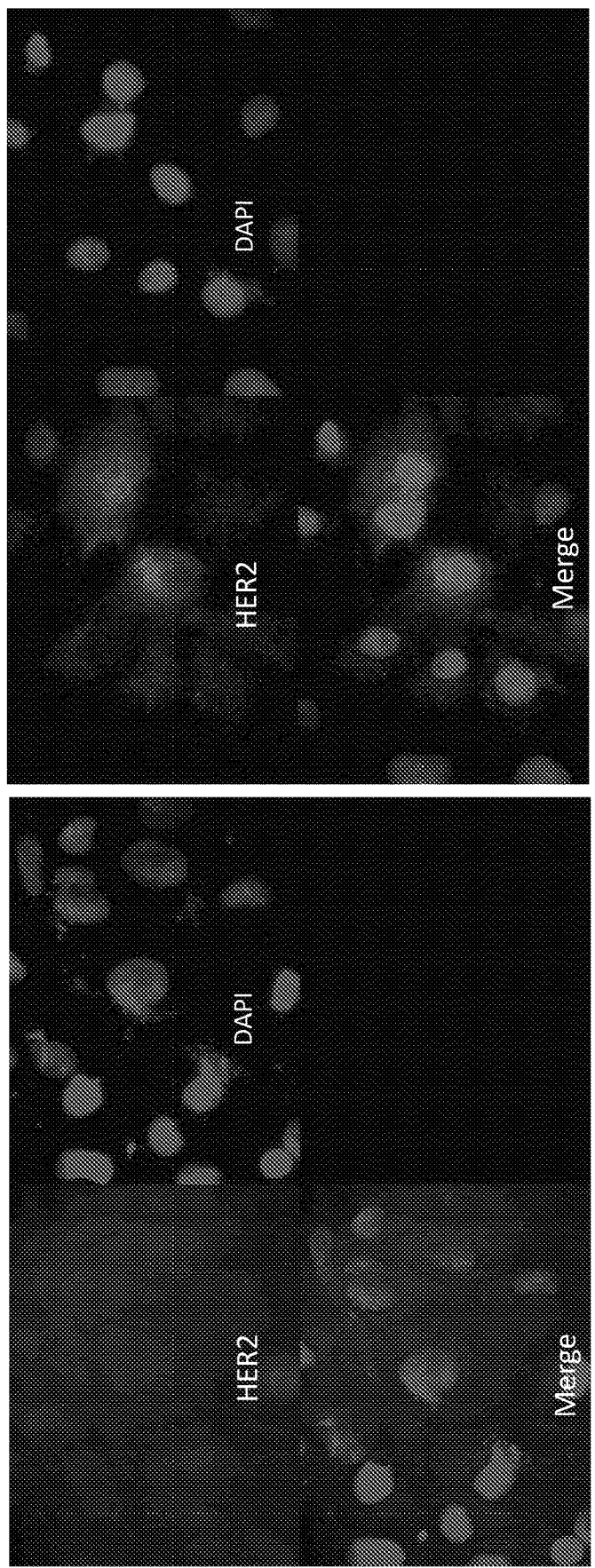

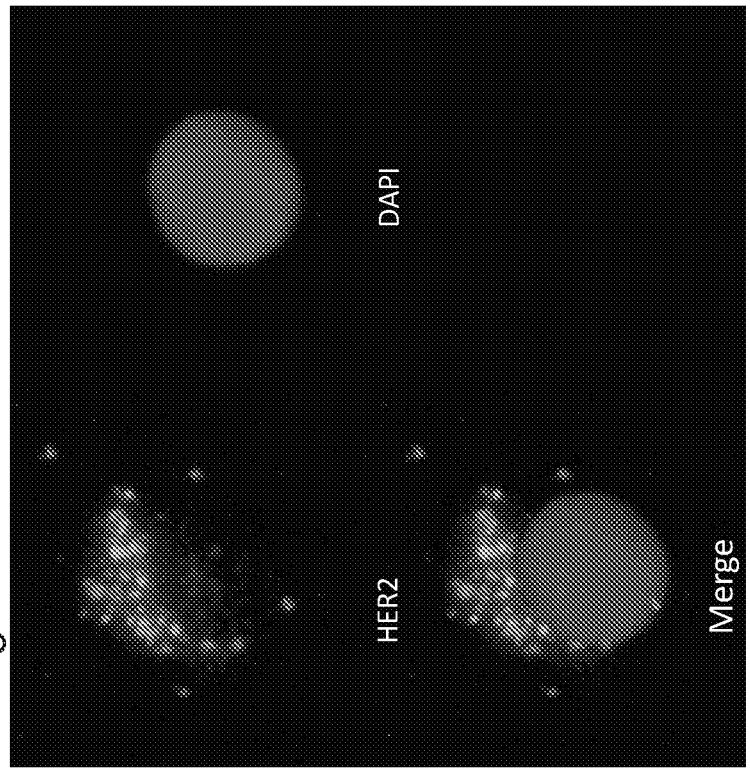
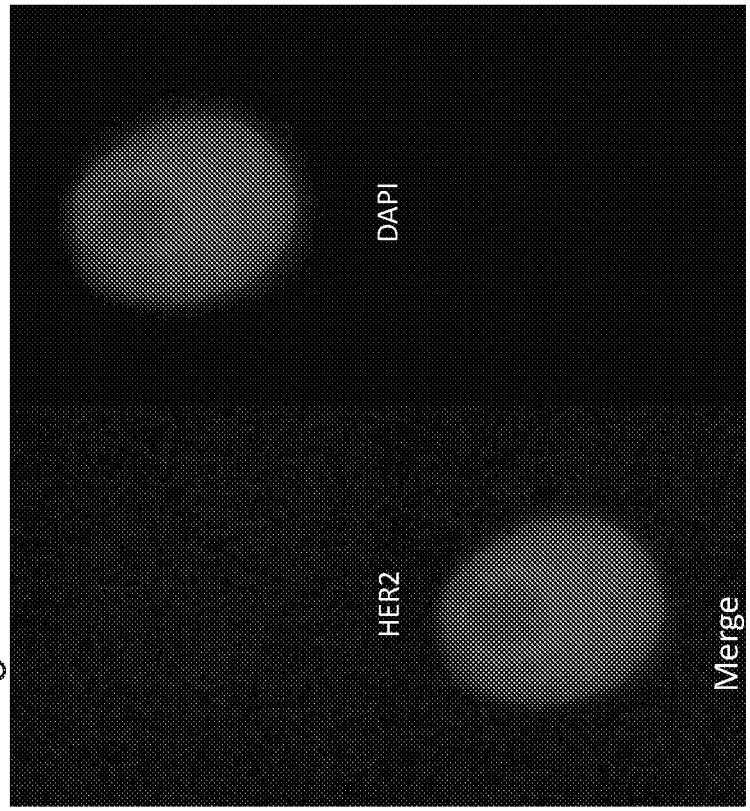

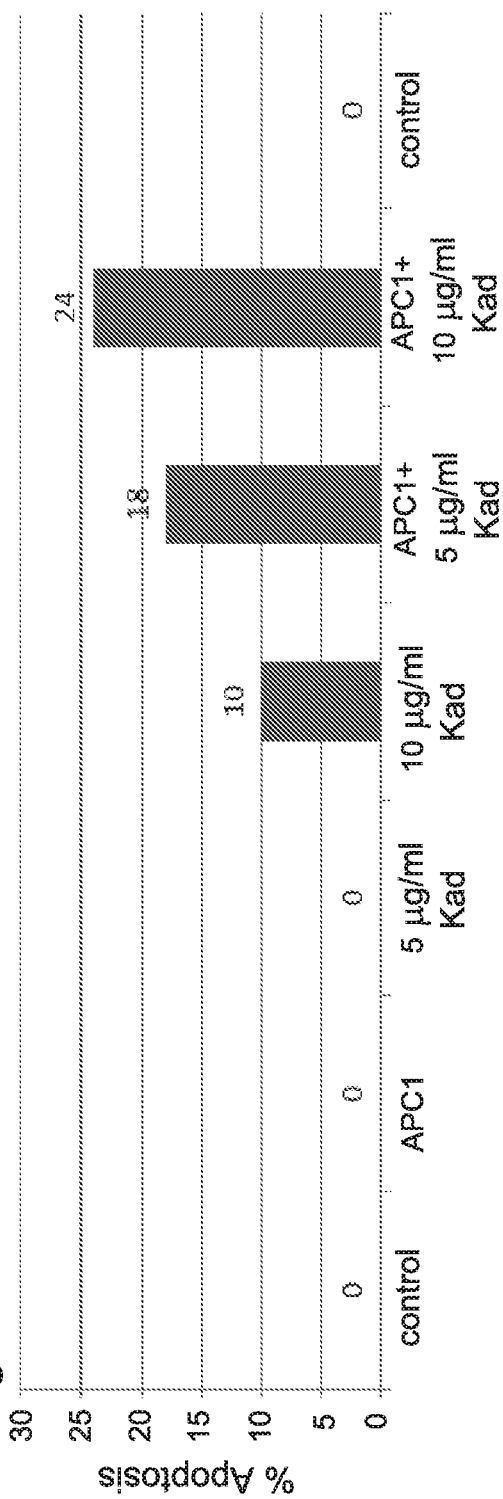
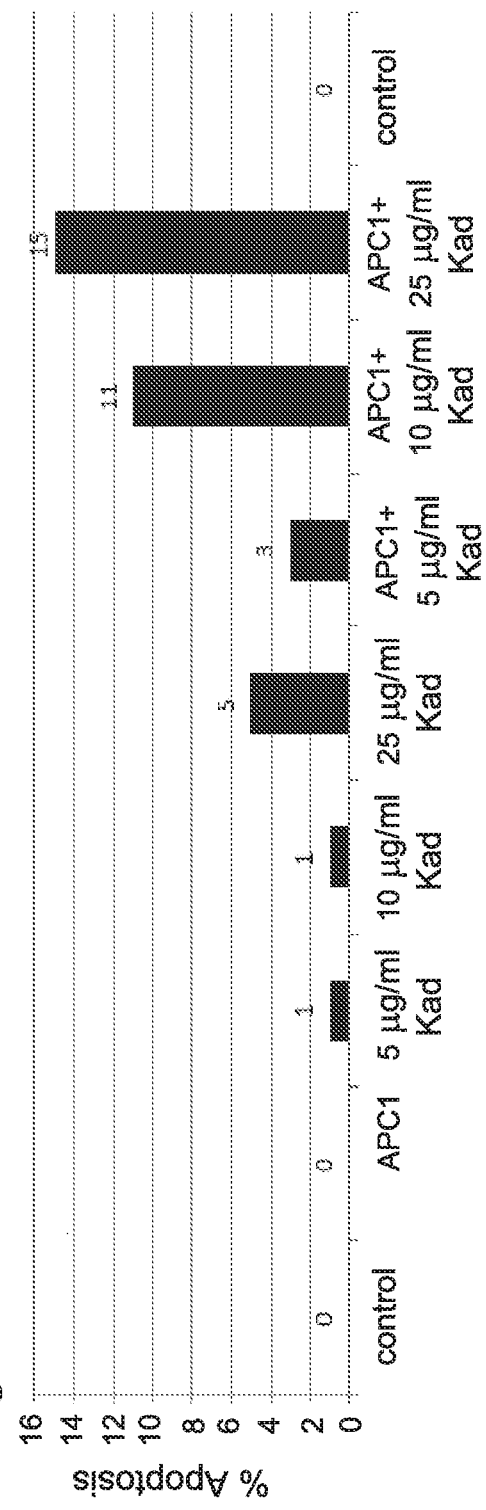
Fig. 5A
Fig. 5B

SEQUENCE LISTING

```
<160> NUMBER OF SEQ ID NOS: 3

<210> SEQ ID NO 1
<211> LENGTH: 14
<212> TYPE: PRT
<213> ORGANISM: Artificial Sequence
<220> FEATURE:
<223> OTHER INFORMATION: C terminal peptide of KTPAF50

<400> SEQUENCE: 1

Glu Lys Gly Ala Ala Phe Ser Pro Ile Tyr Pro Arg Arg Lys
1               5                   10

<210> SEQ ID NO 2
<211> LENGTH: 74
<212> TYPE: PRT
<213> ORGANISM: Homo sapiens

<400> SEQUENCE: 2

Met Pro Gly His Ser Arg Leu Leu Ser Ile Leu Val Ser Gly Leu Cys
1               5                   10                  15

Val Val Gly Ser Ser Ile Gly Val Leu Arg Arg Arg Glu Gln Ala Glu
                20                  25                  30

Arg Gly Ser Arg Arg Cys Ala Ile Ala Gly Glu Glu Arg Ala Met Leu
            35                  40                  45

Ser Pro Ser Pro Leu Pro Glu Thr Pro Phe Ser Pro Glu Lys Gly Ala
        50                  55                  60

Ala Phe Ser Pro Ile Tyr Pro Arg Arg Lys
65                  70

<210> SEQ ID NO 3
<211> LENGTH: 50
<212> TYPE: PRT
<213> ORGANISM: Homo sapiens

<400> SEQUENCE: 3

Leu Arg Arg Arg Glu Gln Ala Glu Arg Gly Ser Arg Arg Cys Ala Ile
1               5                   10                  15

Ala Gly Glu Glu Arg Ala Met Leu Ser Pro Ser Pro Leu Pro Glu Thr
                20                  25                  30

Pro Phe Ser Pro Glu Lys Gly Ala Ala Phe Ser Pro Ile Tyr Pro Arg
            35                  40                  45

Arg Lys
    50
```

METHOD OF SENSITIZING CANCER CELLS TO ANTI-CANCER TREATMENT

SEQUENCE LISTING

The Sequence Listing submitted in text format (.txt) filed on Nov. 14, 2019, named "SequenceListing.txt", created on Nov. 14, 2019 (2 KB), is incorporated herein by reference.

TECHNOLOGICAL FIELD

The present disclosure relates to the treatment of cancer. More specifically, the present disclosure relates to compositions, methods and kits for sensitizing cancer cells to anti-cancer treatment.

BACKGROUND ART

References considered to be relevant as background to the presently disclosed subject matter are listed below:
 [1] Yao, H. et al. 2016, *Oncotarget*, DOI: 10.18632/oncotarget.12284.
 [2] Andre, F. and Zielinski, C. C. 2012, *Annals of Oncology* 23 (Supplement 6): vi46-vi51, 2012.
 [3] WO 2009/083968.
 [4] Sandler, T. et al. 2010, Recent Advances in Clinical Medicine, ISSN: 1790-5125, ISBN: 978-960-474-165-6.

Acknowledgement of the above references herein is not to be inferred as meaning that these are in any way relevant to the patentability of the presently disclosed subject matter.

BACKGROUND

There are over 100 types of cancer and accordingly, many types of cancer treatment. Some of the current anticancer therapies have incomplete effectiveness because they were designed assuming metastatic tumors behave similarly in different organs. In addition, cytotoxic chemotherapy or radiotherapy of cancer is limited by serious, sometimes life-threatening, side effects that arise from toxicities to sensitive normal cells. Therefore there is an ongoing effort to develop targeted therapies that recognize tumor-associated antigens.

Breast cancer is the most commonly encountered form of cancer and the second leading cause of cancer-related mortality among women world-wide, accounting for around 40,000 deaths in the USA during 2015. Every year, an estimated 1 to 1.3 million breast cancer cases are diagnosed worldwide. Of these, approximately 15-20% belong to the triple-negative breast cancer (TNBC) subtype (1).

TNBC is defined by the lack of expression of estrogen receptor (ER) and progesterone receptor (PR) and the lack of expression or amplification of human epidermal growth factor receptor 2 (HER2).

Treatment of TNBC is presently based on a number of agents that are approved for general breast cancer patients. This treatment includes anthracyclines, taxanes, platinum-based regimens and anti-angiogenic therapies, to name but a few (2).

However, in the absence of specific targets for treatment, TNBC is currently considered as an aggressive cancer subtype with limited treatment options and very poor prognosis following treatment with standard regimens. There is currently an unmet need for new effective therapies, in particular for patients with metastatic disease (2).

A peptide termed "KTPAF50" and fragments thereof were previously shown to be associated with a decrease in the viability and with inhibition of proliferation of various types of cancer cells in vitro and in mice (3, 4).

GENERAL DESCRIPTION

The present disclosure provides by one of its aspects a method for treatment of cancer in a patient in need thereof, said method comprising administering to said patient an isolated polypeptide comprising the amino acid sequence denoted by SEQ ID NO: 1 or a functional fragment or derivative thereof and at least one anti-cancer agent.

In some embodiments the isolated polypeptide according to the present disclosure increases the responsiveness of said patient to said at least one anti-cancer agent. In further embodiments the isolated polypeptide according to the present disclosure modulates expression of at least one cellular moiety in cancer cells in said patient. In still further embodiments the isolated polypeptide according to the present disclosure increases or decreases expression of at least one cellular moiety in cancer cells in said patient.

In some embodiments the cellular moiety as defined by the present disclosure is present on the cell surface of said cancer cells or is an intra-cellular moiety. In other embodiments the cellular moiety as defined by the present disclosure is a receptor, a polypeptide, an enzyme, a transcription factor or an adapting molecule. In specific embodiments the cellular moiety as defined by the present disclosure is a cell surface receptor.

In yet further specific embodiments the isolated polypeptide according to the present disclosure increases expression of at least one cellular moiety in cancer cells in said patient and the cellular moiety as herein defined is a receptor.

In some embodiments the cellular moiety according to the present disclosure is at least one of human epidermal growth factor receptor 2 (HER2/neu receptor), estrogen receptor (ER), progesterone receptor (PR), glutathione (GSH), epidermal growth factor receptor (EGFR), androgen receptor, B-lymphocyte antigen cluster of differentiation CD20 (CD20), cluster of differentiation 33 (CD33), programmed cell death ligand (PD-L) or ST2 receptor.

In other embodiments the at least one anti-cancer agent according to the present disclosure directly or indirectly interacts with said at least one cellular moiety. In further embodiments the anti-cancer agent according to the present disclosure is an immunotherapy, a chemotherapeutic agent, a signal transduction inhibitor, a receptor inhibitor, a gene expression modulator, an apoptosis inducer, an angiogenesis inhibitor, a hormone therapy, a metabolic inhibitor, an anti-autophagy agent, an endoplasmic reticulum stress inducer, a reactive oxygen species (ROS) inducer or a combination thereof.

In some embodiments the at least one anti-cancer agent according to the present disclosure is an immunotherapy, preferably a monoclonal antibody or a conjugated antibody. In other embodiments the monoclonal antibody or a conjugated antibody as herein defined are directed against at least one of HER2, ER or PR.

In other embodiments the at least one anti-cancer agent as herein defined is a receptor inhibitor, preferably an inhibitor of epidermal growth factor receptor (EGFR). In further embodiments the at least one anti-cancer agent according to the present disclosure is a chemotherapeutic agent, preferably doxorubicin or doxorubicin derivative, cisplatin, taxol or a reactive oxygen species (ROS) inducer.

In particular embodiments the patient according to the present disclosure is not responsive to said anti-cancer agent when administered without said isolated polypeptide.

In some embodiments cancer as herein defined is at least one of breast cancer, ovarian cancer, prostate cancer, lung cancer, colon cancer, B cell lymphoma, Acute Myeloid Leukemia (AML) or pancreatic cancer. In various embodiments cancer as herein defined is triple negative breast cancer (TNBC).

The present disclosure further provides a method for treatment of triple negative breast cancer (TNBC) in a patient in need thereof, said method comprising administering to said patient an isolated polypeptide comprising the amino acid sequence denoted by SEQ ID NO: 1 or a functional fragment or derivative thereof and at least one anti-cancer agent. In some embodiments the isolated polypeptide defined by the present disclosure increases expression of at least one of human epidermal growth factor receptor 2 (HER2/neu receptor), estrogen receptor (ER) or progesterone receptor (PR) in cancer cells in said patient.

In some embodiments the isolated polypeptide of the present disclosure consists of the amino acid sequence denoted by SEQ ID NO: 1.

In other embodiments the at least one anti-cancer agent as herein defined interacts with Her2/neu receptor, ER or PR. In further embodiments the at least one anti-cancer agent as herein defined is a chemotherapeutic agent, preferably doxorubicin or doxorubicin derivative, cisplatin, taxol or a reactive oxygen species (ROS) inducer.

By another one of its aspects the present disclosure provides a method for sensitizing cancer cells to at least one anti-cancer agent in a patient in need thereof, said method comprising administering to said patient an isolated polypeptide comprising the amino acid sequence denoted by SEQ ID NO: 1 or a functional fragment or derivative thereof, wherein said isolated polypeptide modulates expression of at least one cellular moiety in cancer cells in said patient, thereby sensitizing said cancer cells to said at least one anti-cancer agent. In some embodiments the method for sensitizing cancer cells to at least one anti-cancer agent further comprises administering said at least one anti-cancer agent as herein defined to said patient.

In various embodiments the isolated polypeptide of the present disclosure and/or said at least one anti-cancer agent are comprised in a pharmaceutical composition which optionally further comprises a pharmaceutically acceptable carrier, diluent and/or excipient.

In some embodiments the method according to the present disclosure is wherein isolated polypeptide as herein defined is administered prior to, concomitantly with or after the administration of the at least one an anti-cancer agent of the present disclosure.

By still another one of its aspects the present disclosure provides an isolated polypeptide comprising the amino acid sequence denoted by SEQ ID NO: 1 or a functional fragment or derivative thereof and at least one anti-cancer agent for use in a method for treatment of cancer in a patient in need thereof.

Still further the present disclosure provides an isolated polypeptide comprising the amino acid sequence denoted by SEQ ID NO: 1 or a functional fragment or derivative thereof and at least one anti-cancer agent for use in a method for treatment of triple negative breast cancer (TNBC) in a patient in need thereof.

The present disclosure further provides an isolated polypeptide comprising the amino acid sequence denoted by SEQ ID NO: 1 or a functional fragment or derivative thereof for use in a method for sensitizing cancer cells to at least one anti-cancer agent in a patient in need thereof, wherein said isolated polypeptide modulates expression of at least one cellular moiety in cancer cells in said patient, thereby sensitizing said cancer cells to said at least one anti-cancer agent. In some particular embodiments the isolated polypeptide and the at least one anti-cancer agent for use in a method for sensitizing cancer cells to at least one anti-cancer agent according to the invention is wherein said method further comprises administering said at least one anti-cancer agent to said patient.

Still further the present disclosure provides a kit comprising:
(i) an isolated polypeptide comprising the amino acid sequence denoted by SEQ ID NO: 1 or a functional fragment or derivative thereof and optionally a pharmaceutically acceptable carrier, diluent and/or excipient;
(ii) an anti-cancer agent and optionally a pharmaceutically acceptable carrier, diluent and/or excipient.

In some embodiments the kit according to the present disclosure further comprises instructions for use.

In various embodiments the kit as herein defined is for use in a method of treating cancer in a patient in need thereof.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

Figures are showing FACS analysis graphs of HER2 receptor expression on MDA-MB-231 cells without treatment (control cells, FIG. 1A) or upon treatment with two doses of APC1 at 100 µg/ml (FIG. 1B) and at 250 µg/ml (FIG. 1C). Cells were incubated for 24 hours in the presence of the first administration and 72 hours in the presence of the second administration. FIG. 1D shows a positive control of HER2 expression in the absence of APC1 on N87 cells.

FIG. 2A-FIG. 2B: Immunofluorescence of MDA-MB-231 cells administered with APC1

Figures show immunofluorescence micrographs of MDA-MB-231 cells incubated for 48 hours in the absence (FIG. 2A) or in the presence (FIG. 2B) of a single dose of APC1 (250 µg/ml). HER2 designates immunofluorescence using an antibody directed to HER2; DAPI designates immunofluorescence of DAPI staining: and Merge designates immunofluorescence of both HER2 and DAPI.

FIG. 3A-FIG. 3B: Immunofluorescence of MDA-MB-231 cells administered with multiple doses of APC1

Figures show immunofluorescence micrographs of MDA-MB-231 cells incubated for 144, 96 and 72 hours in the absence (FIG. 3A) or in the presence (FIG. 3B) of multiple doses of APC (250 µg/ml each). HER2 designates immunofluorescence using an antibody directed to HER2; DAPI designates immunofluorescence of DAPI staining; Merge designates immunofluorescence of both HER2 and DAPI.

Figure 4A:
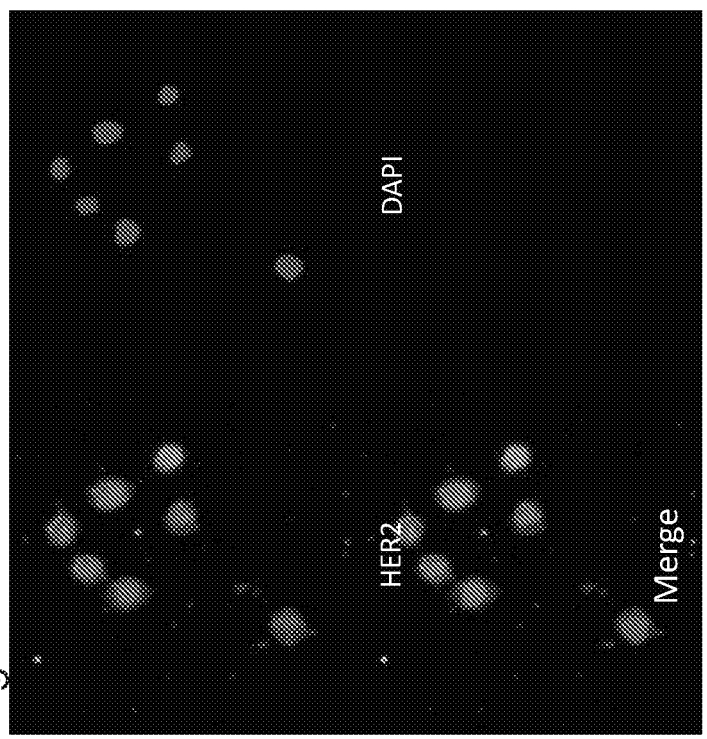
Figure 4B:
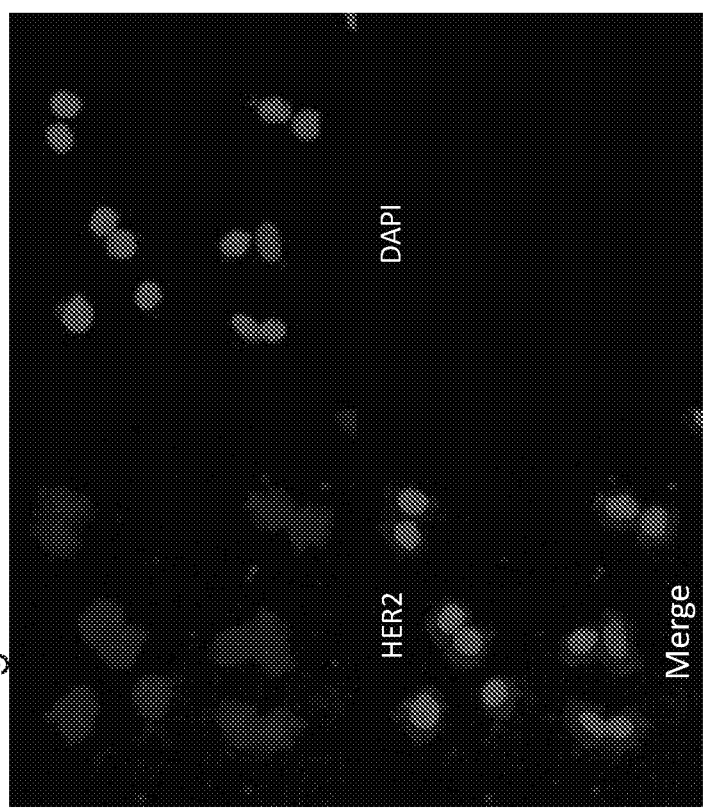

FIG. 4A-FIG. 4B: Immunofluorescence of MDA-MB-468 cells administered with APC1

Figures show immunofluorescence micrographs of MDA-MB-468 cells incubated for 24 and 72 hours in the absence (FIG. 4A) or in the presence (FIG. 4B) of multiple doses of APC1 (100 µg/ml each). HER2 designates immunofluorescence using an antibody directed to HER2; DAPI designates immunofluorescence of DAPI staining: Merge designates immunofluorescence of both HER2 and DAPI.

FIG. 5A-FIG. 5B: Analysis of Apoptosis in MDA-MB-231 cells administered with APC1 and Kadcyla Figures show bar graphs of percentage of apoptosis in MDA-MB-231 cells administered first with APC1 (two doses of 250 μg/ml, each followed by incubations of 24 and 72 hours, respectively) and then with Kadcyla at 5 or 10 μg/ml for 72 hours (FIG. 5A) or at 5, 10 or 25 μg/ml for 72 hours (FIG. 5B). Cells were also incubated in the presence of APC1, as detailed above, or Kadcyla at the indicated concentrations. Abbreviations: Control, no treatment; Kad, Kadcyla.

Figure 6:
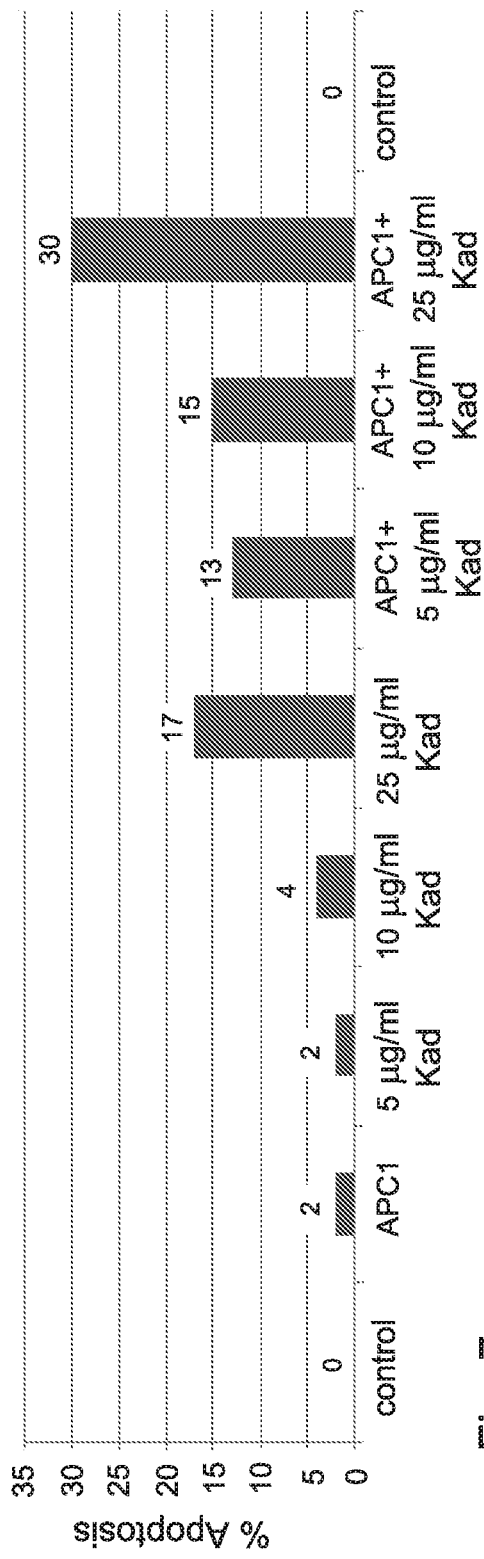

FIG. 6: Analysis of Apoptosis in MDA-MB-231 cells administered with APC1 and Kadcyla under prolonged incubation A bar graph showing the percentage of apoptosis in MDA-MB-231 cells administered first with APC1 (two doses of 250 μg/ml, each, followed by incubations of 24 and 72 hours, respectively) and then with Kadcyla at 5, 10 or 25 μg/ml for 96 hours. Cells were also incubated in the presence of APC1, as detailed above, or Kadcyla at the indicated concentrations. Abbreviations: Control, no treatment; Kad, Kadcyla.

Figure 7:
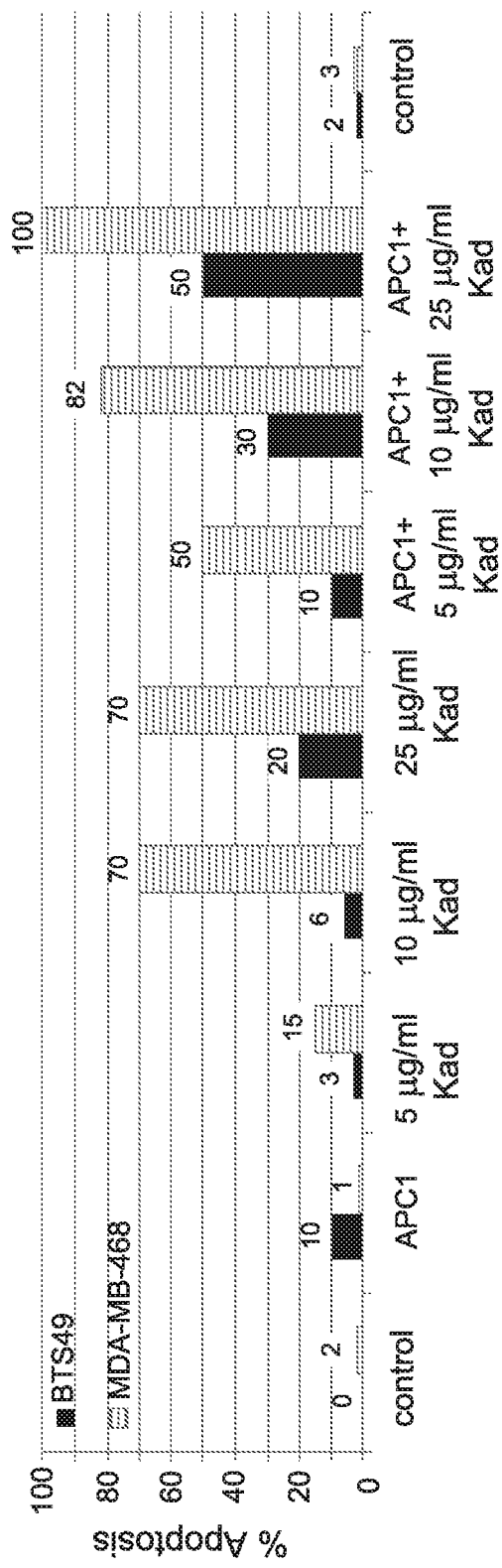

FIG. 7: Analysis of Apoptosis in BTS49 and MDA-MB-468 cells administered with APC1 and Kadcyla A bar graph showing the percentage of apoptosis in BTS49 and MDA-MB-468 cells administered first with APC1 (two doses of 250 μg/ml, each, followed by incubations of 24 and 72 hours, respectively) and then with Kadcyla at 5, 10 or 25 μg/ml for 96 hours. Cells were also incubated in the presence of APC1, as detailed above, or Kadcyla at the indicated concentrations. Abbreviations: Control, no treatment; Kad, Kadcyla.

Figure 8B:
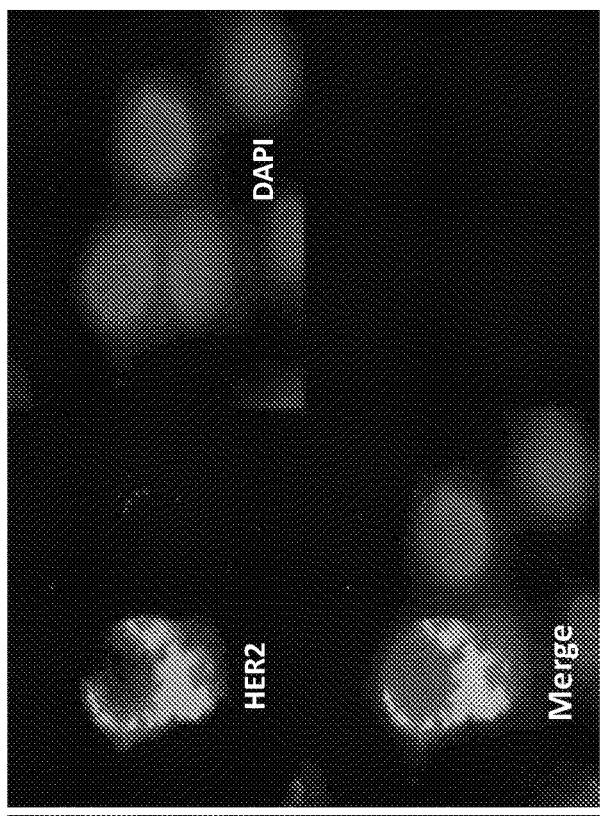
Figure 8A:
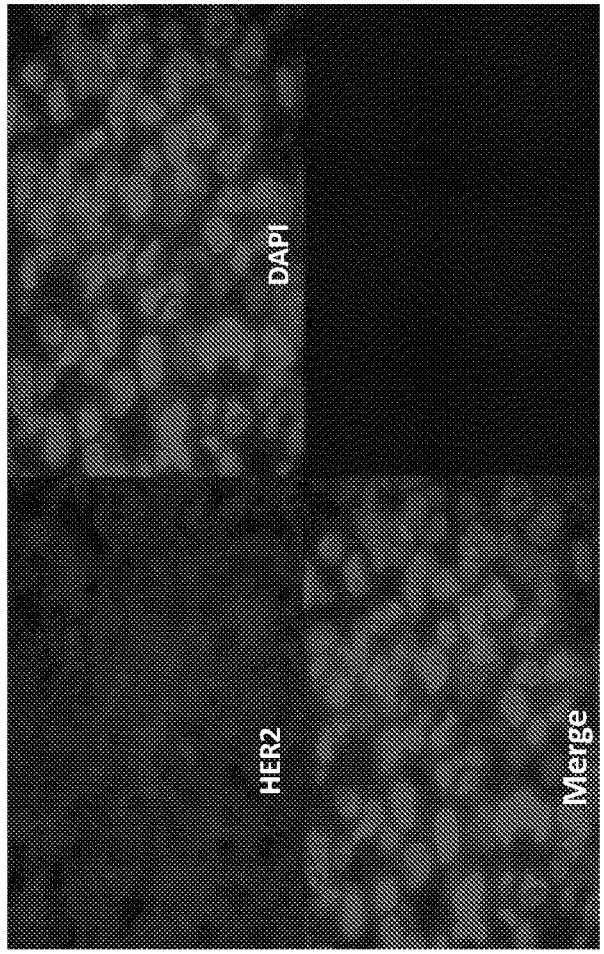

FIG. 8A-FIG. 8B: HER2 immunohistochemistry of MDA-MB-231 tumors from nude mice

Figures show immunofluorescence micrographs of MDA-MB-231 tumor sections obtained from Balb/C nude mice that were subjected to MDA-MB-231 tumor injection and were administered with multiple administrations of APC1 (at doses of 350 μg/mouse each). HER2, immunofluorescence using an antibody directed to HER2; DAPI, immunofluorescence of DAPI staining, Merge designates immunofluorescence of both HER2 and DAPI.

Figure 9:
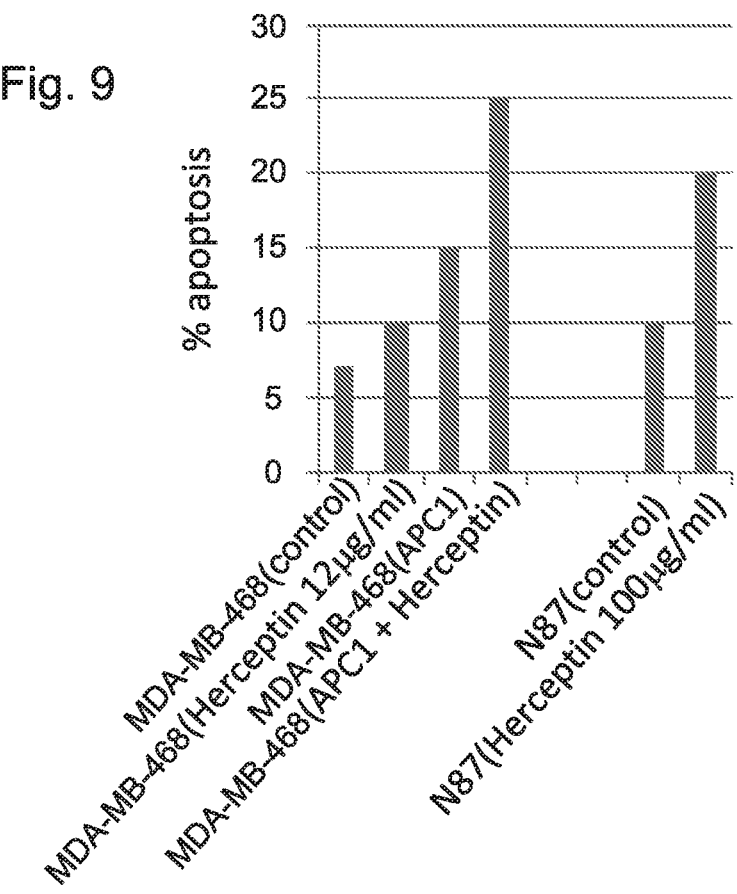

FIG. 9: Analysis of Apoptosis in MDA-MB-468 cells administered with APC1 and Herceptin A bar graph showing the level of apoptosis in MDA-MB-468 cells without any treatment (control), upon administration of Herceptin (12 μg/ml), APC1 (250 μg/ml) or upon administration of APC and Herceptin at the above amounts. The level of apoptosis is also shown for N87 cell in the absence and in the presence of Herceptin (at 100 μg/ml).

Figure 10:
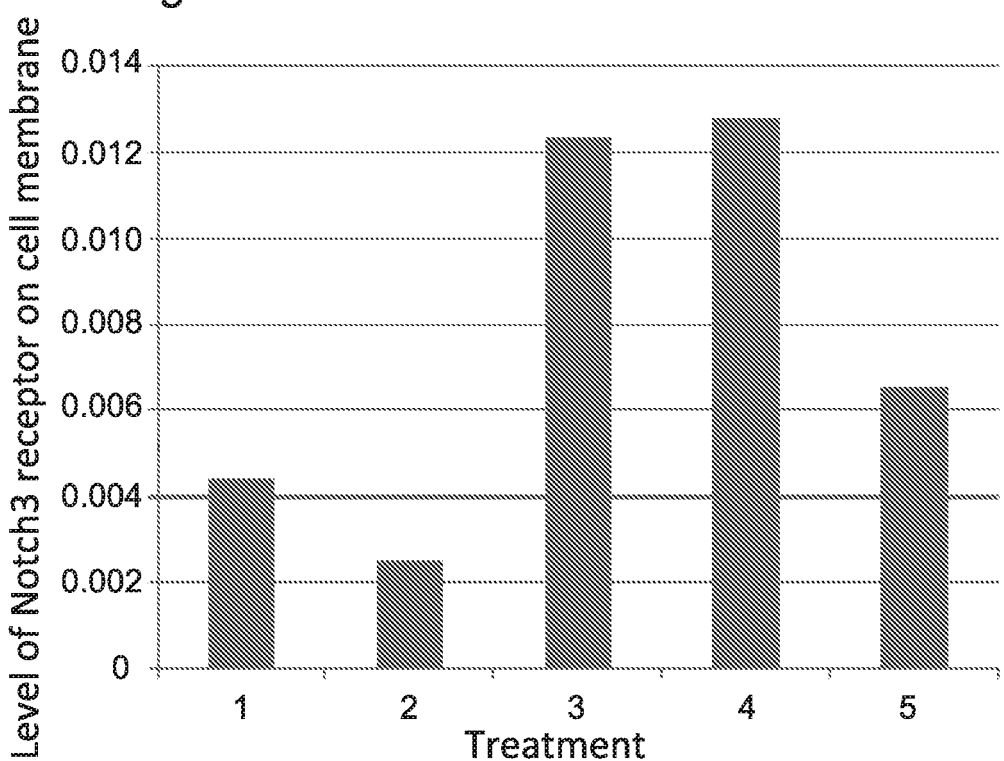

FIG. 10: The level of the Notch3 receptor on the cell membrane of MDA-MB-231 cells administered with APC1

A bar graph showing the level of the Notch3 receptor on the cell membrane of MDA-MB-231 cells (arbitrary density units are shown) administered with APC1 (250 μg/ml) for 1 hour (lane 2), 3 hours (lane 3), 5 hours (lane 4) or 24 hours (lane 5). Lane 1 is a control.

Figure 11A:
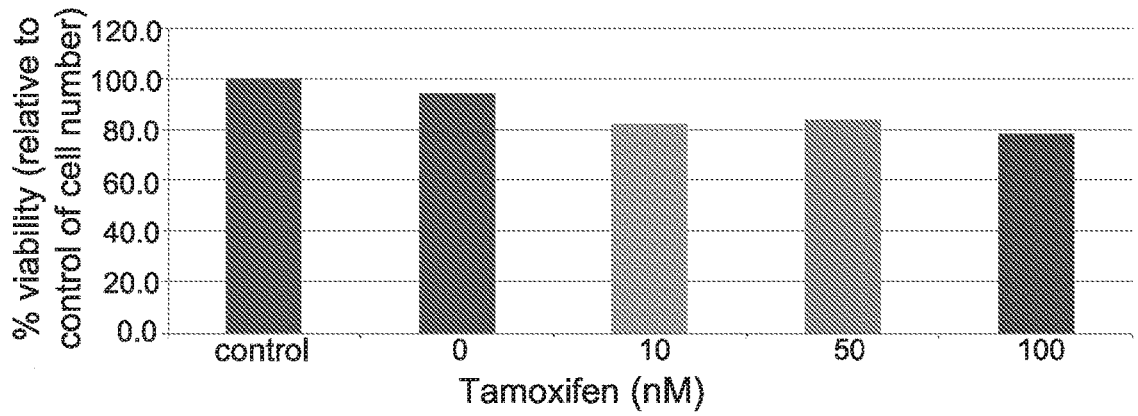
Figure 11B:
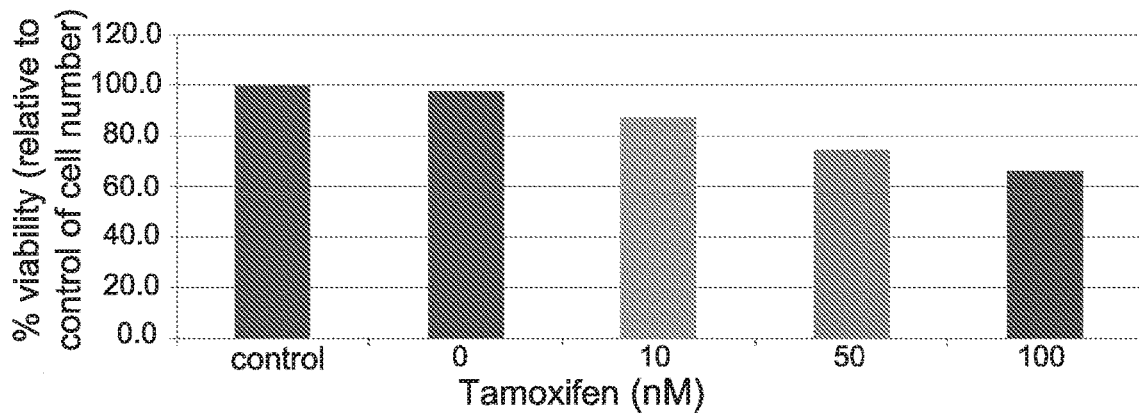
Figure 11C:
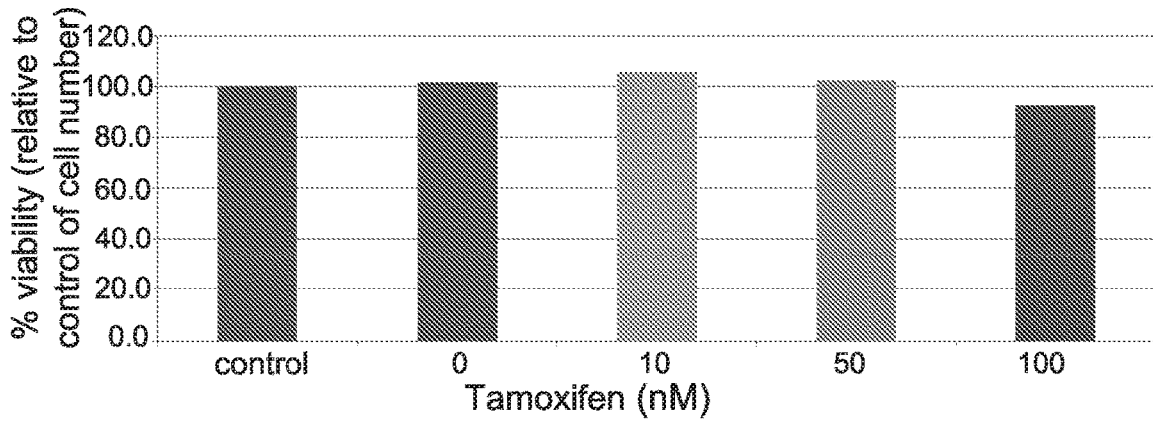

FIG. 11A-FIG. 11C: Viability of MDA-MB-231 cells administered with APC1 and tamoxifen (24 hours incubation)

Bar graphs showing cell viability (using resazurin assays) of MDA-MB-231 cells (FIG. 11A), APC1-treated MDA-MB-231 cells (FIG. 11B) and MDA-MB-231 cells treated with anti-PRT3 (FIG. 11C) that were incubated for 24 hours in the presence of culture medium (indicated as "0") or 10, 50 or 100 nM Tamoxifen. Control, no treatment.

Figure 12A:
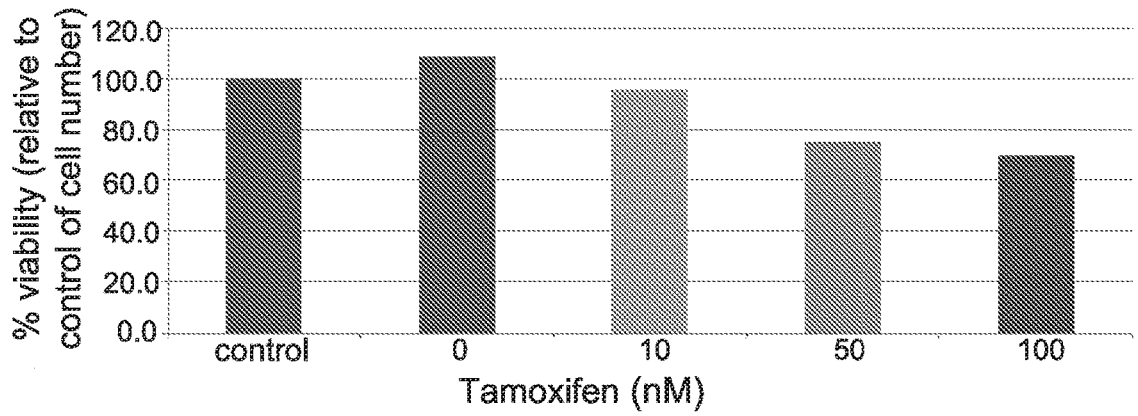
Figure 12B:
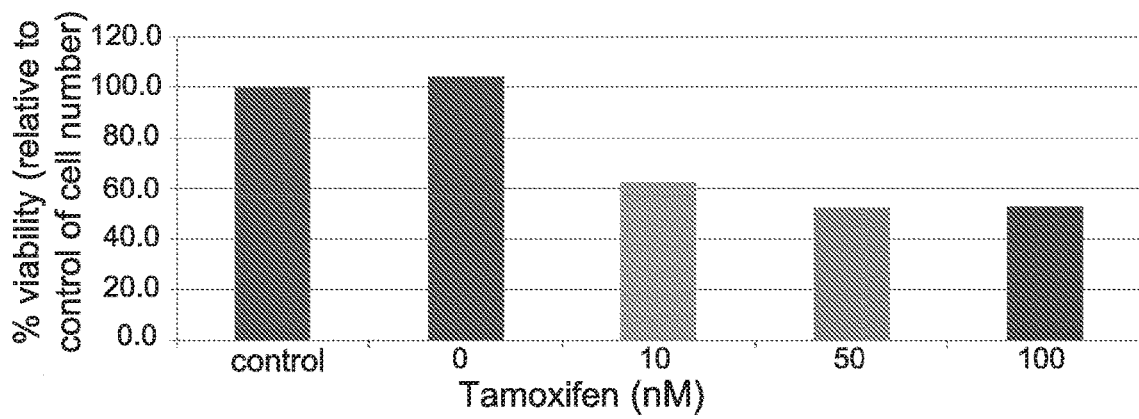
Figure 12C:
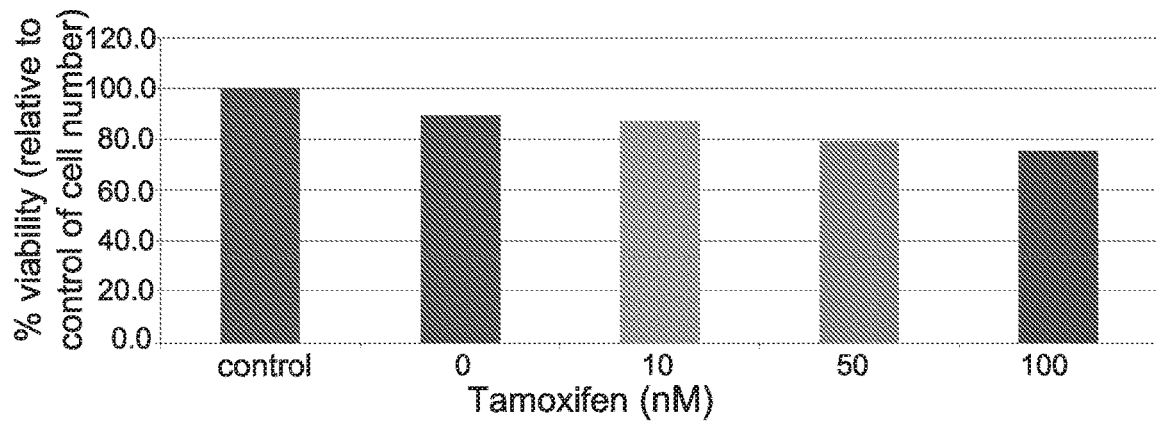

FIG. 12A-FIG. 12C: Analysis of viability of MDA-MB-231 cells administered with APC1 and tamoxifen (48 hours incubation)

Bar graphs showing cell viability (resazurin assays) of MDA-MB-231 cells (FIG. 12A), APC1-treated MDA-MB-231 cells (FIG. 12B) or MDA-MB-231 cells treated with anti-PRT3 (FIG. 12C) incubated for 48 hours in the presence of culture medium (indicated as "0") or 10, 50 or 100 nM Tamoxifen. Control, no treatment.

Figure 13:
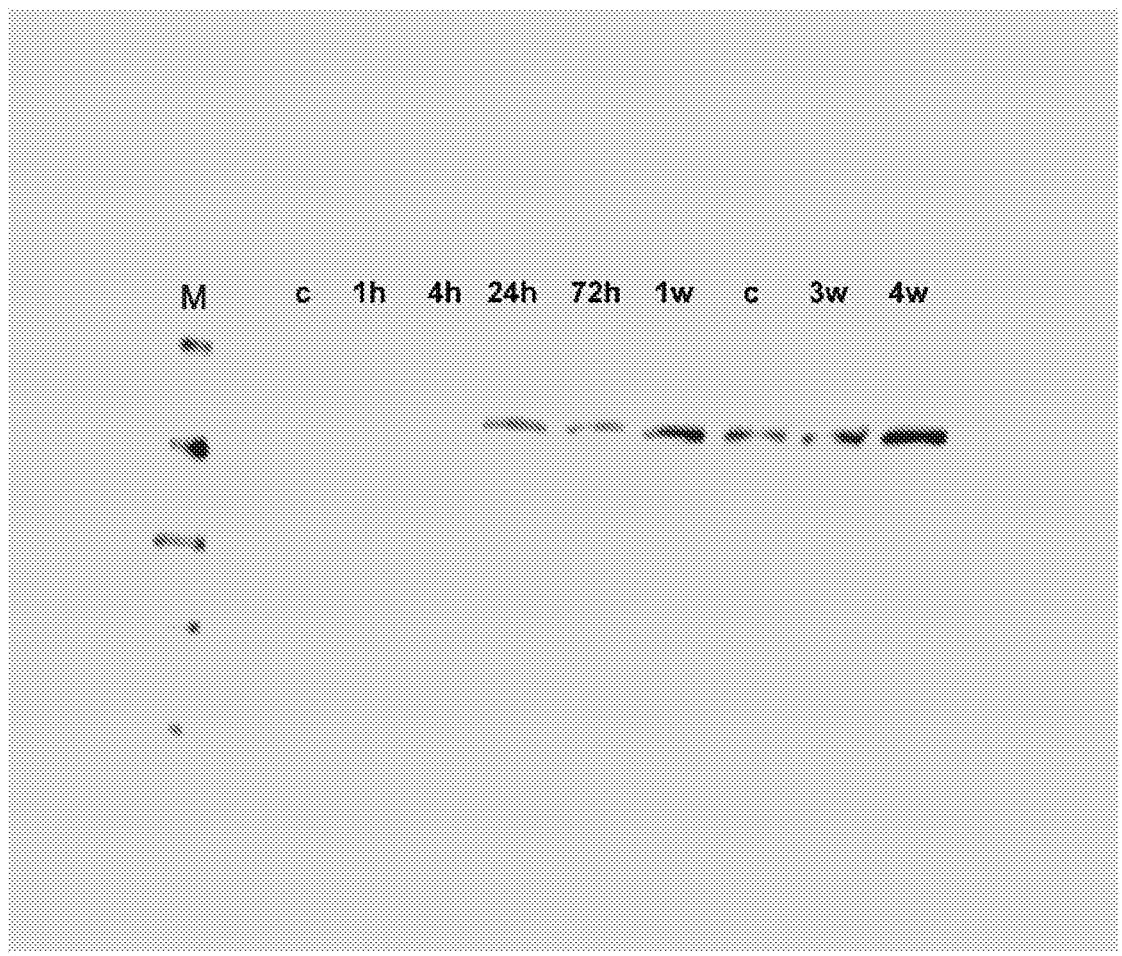

FIG. 13: Western blot analysis of expression of ERalpha in MDA-MB-231 cells incubated with APC1

The figure shows a western blot analysis assayed with an anti-estrogen receptor alpha (ER alpha) antibody of estrogen alpha receptor expression at the indicated time points in MDA-MB-231 cells treated with APC1 (250 μg/ml) once a week for one week (lanes 3 to 7 from the left) or twice a week for 3 or 4 weeks (lanes 9, 10 from the left). Abbreviations: M, protein parker; c, control; h, hour; w, week.

Figure 14A:
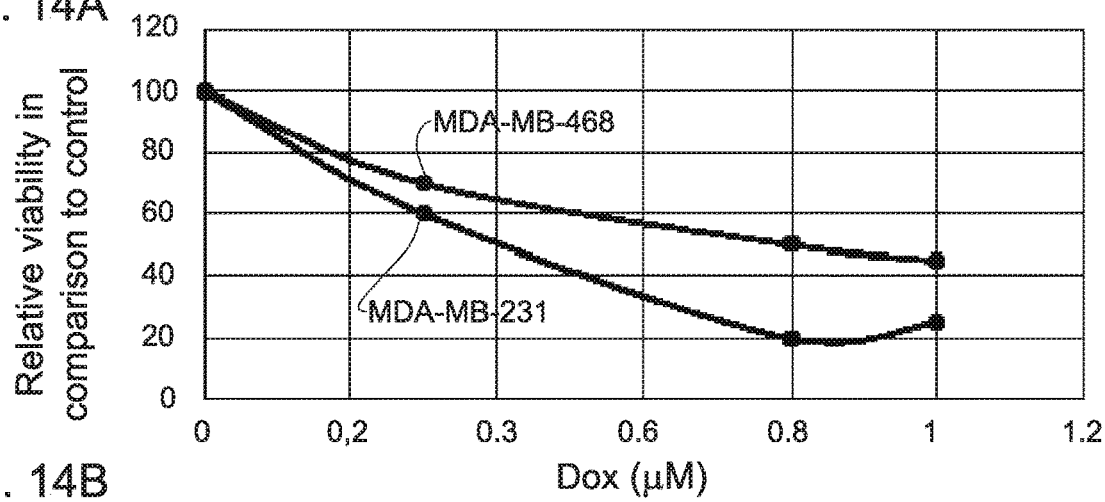
Figure 14B:
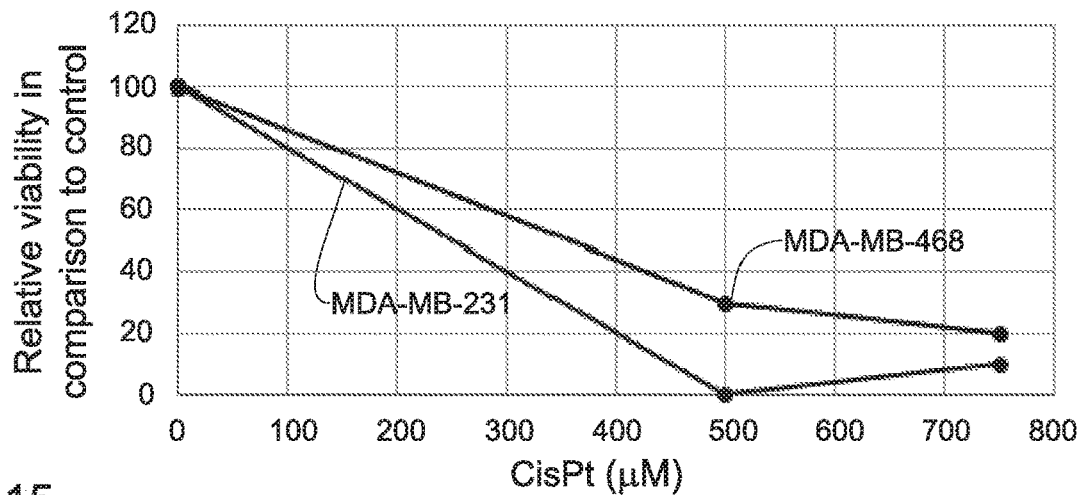

FIG. 14A-FIG. 14B: Treatment of TNBC cells with APC1 and chemotherapy

The graphs show relative cell viability of MDA-MB-231 and MDA-MB-468 cells pre-treated with APC1 and then incubated in the presence of doxorubicin (FIG. 14A) or cisplatin (FIG. 14B) at the indicated concentrations. Abbreviations: Dox, doxorubicin; CisPt, cisplatin.

Figure 15:
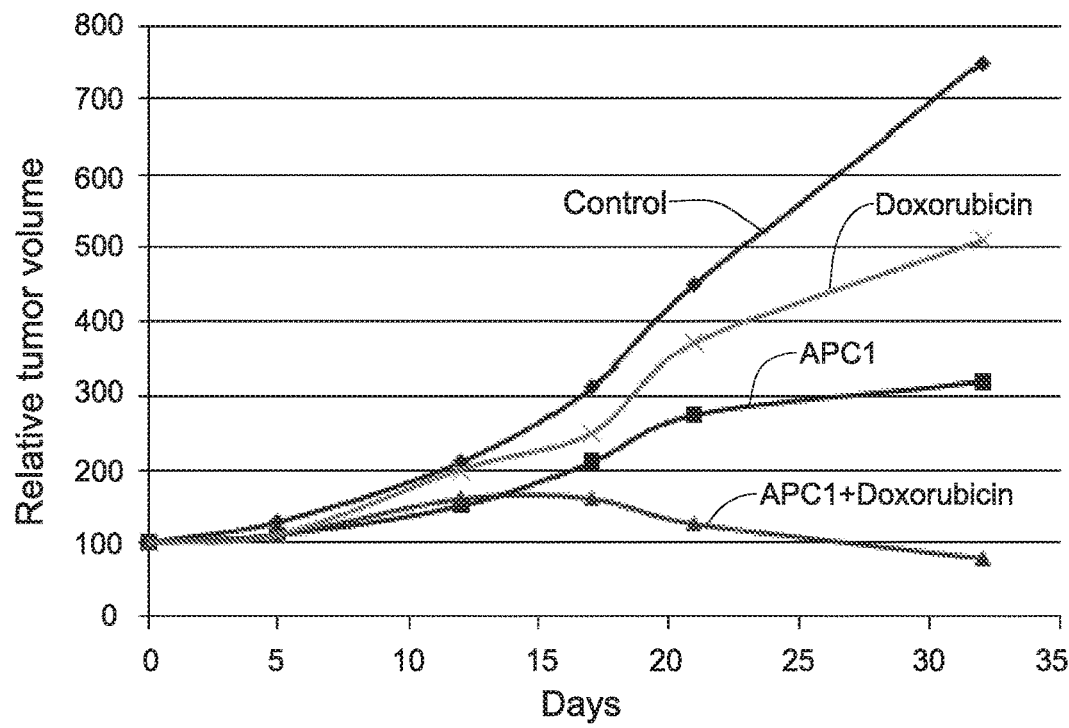

FIG. 15: The effect of APC1 and doxorubicin on human TNBC tumors

The graph shows relative tumor volume in nude mice inoculated with TNBC cells and treated with APC1 (at 15 mg/kg, 3 times per week for up to 5 weeks), doxorubicin (at 3 mg/kg, once a week) or with APC1 and doxorubicin (APC at 15 mg/kg, twice per week and doxorubicin at 3 mg/kg, once a week). The control mice group was treated with saline.

Figure 16:
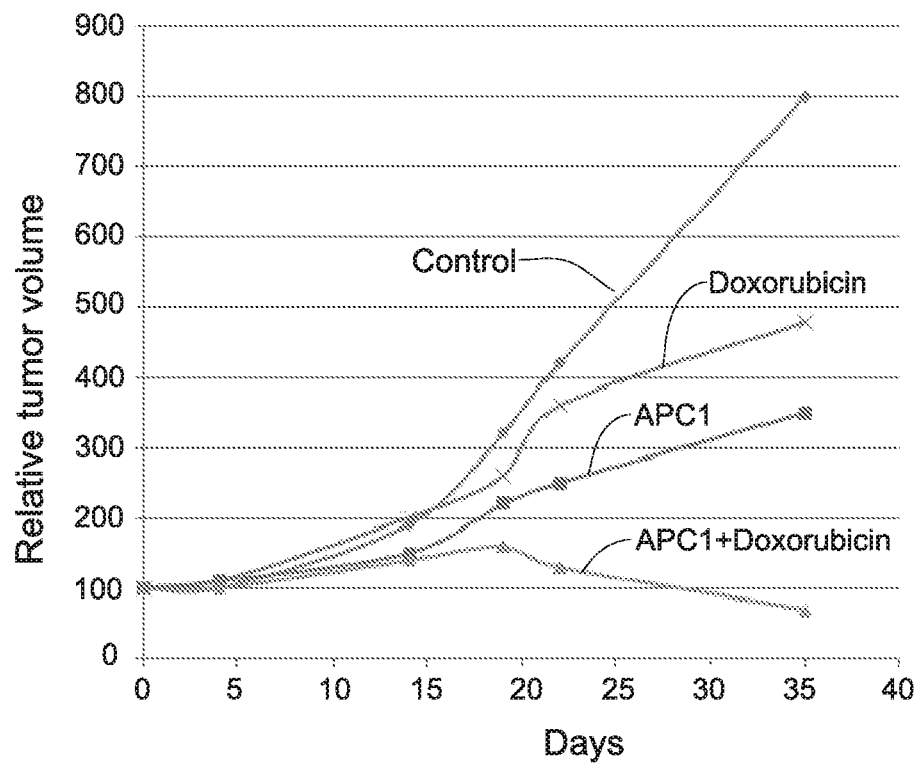

FIG. 16: The effect of APC1 and doxorubicin on human ovarian cancer tumors

The graph shows relative tumor volume in nude mice inoculated with human ovarian cancer cells (OV90) treated with APC1 (at 15 mg/kg, 3 times per week for up to 5 weeks), doxorubicin (at 3 mg/kg, once a week) or with APC1 and doxorubicin (APC1 at 15 mg/kg, twice per week and doxorubicin at 3 mg/kg, once a week). The control mice group was treated with saline.

Figure 17:
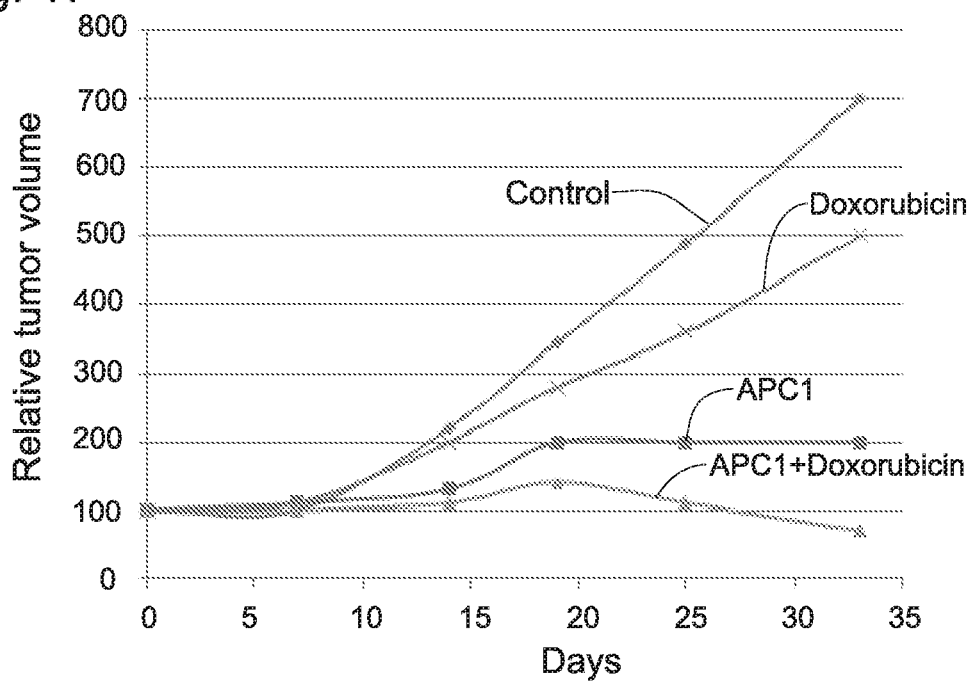

FIG. 17: The effect of APC1 and doxorubicin on human pancreatic cancer tumors

The graph shows relative tumor volume in nude mice inoculated with human pancreatic cancer cells (Panc1) treated with APC1 (at 15 mg/kg, 3 times per week for up to 5 weeks), doxorubicin (at 3 mg/kg, once a week) or with APC1 and doxorubicin (APC1 at 15 mg/kg, twice per week and doxorubicin at 3 mg/kg, once a week). The control mice group was treated with saline.

Figure 18A:
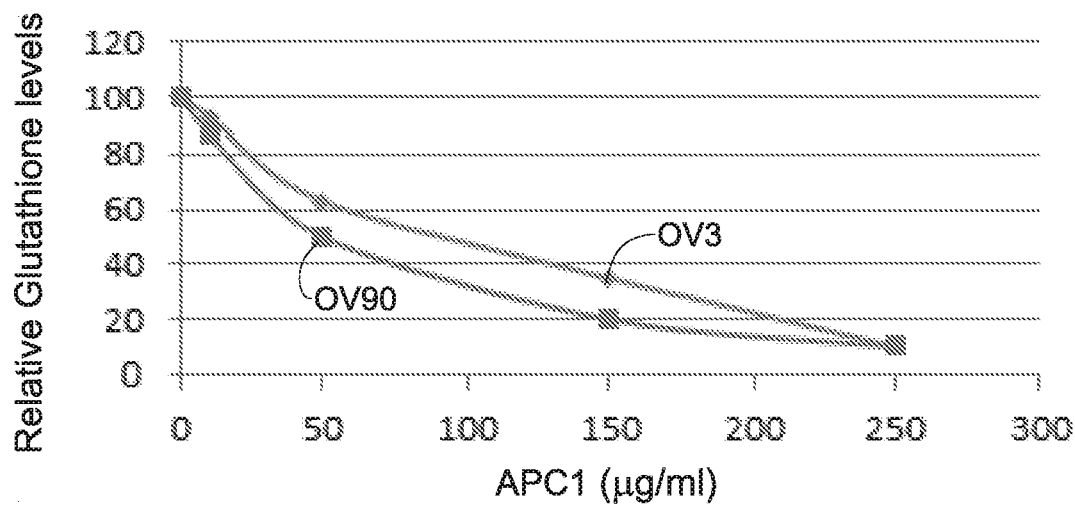
Figure 18B:
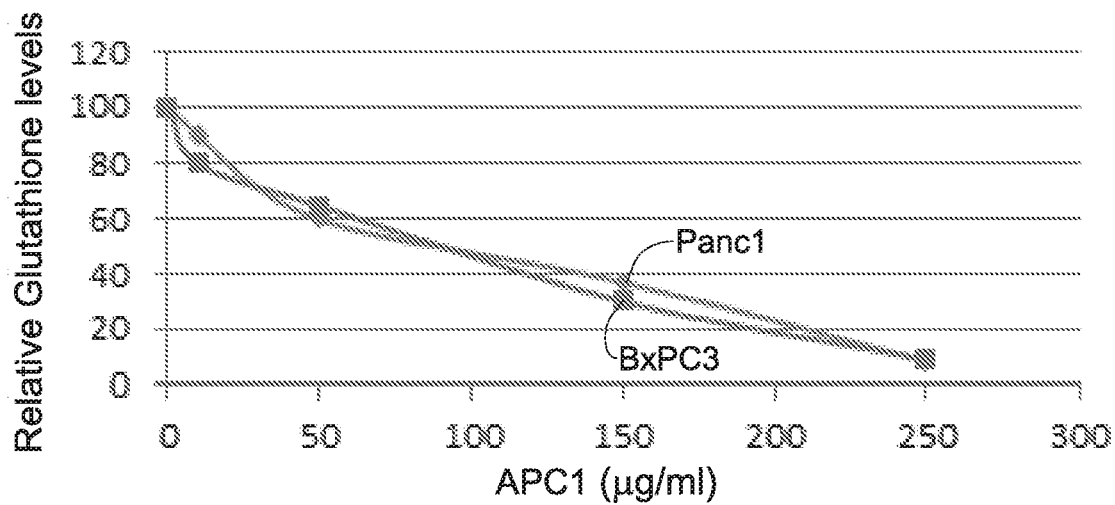
Figure 18C:
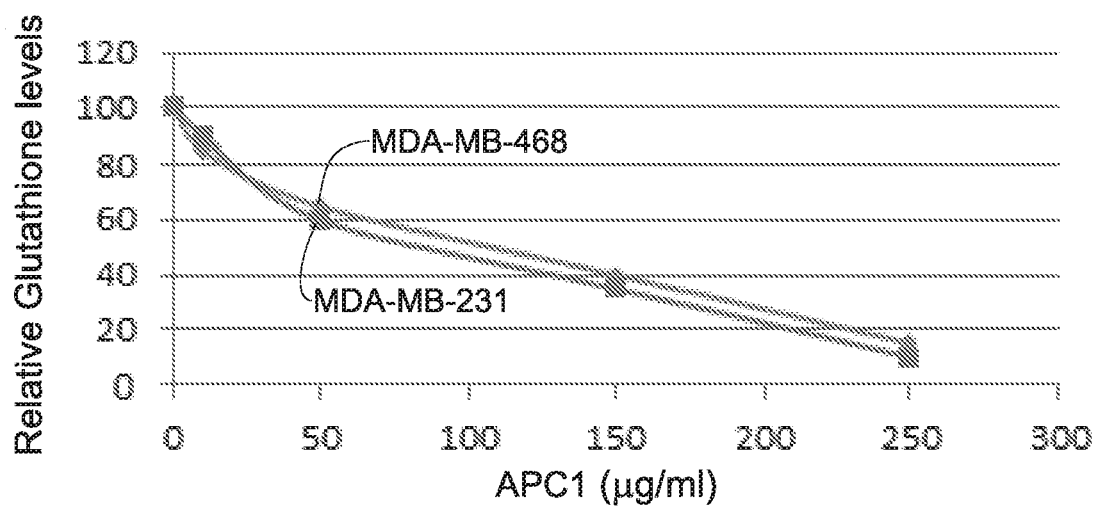

FIG. 18A-FIG. 18C: The effect of APC1 on glutathione levels in human cancer cells The graphs show relative glutathione levels in human ovarian cancer cells (FIG. 18A), human pancreatic cancer cells (FIG. 18B) and human TNBC cells (FIG. 18C) treated with APC1 at the indicated concentrations.

DETAILED DESCRIPTION OF EMBODIMENTS

The present invention is based on the surprising finding that administration of the polypeptide termed herein "APC1", which consists of the amino acid sequence EKGAAFSPIYPRRK (denoted by SEQ ID NO: 1) increased sensitivity of cancer cells to a broad spectrum of anti-cancer agents and may thus be used as an augmenter of the therapeutic effect of anti-cancer agents (drugs).

As detailed in the Examples below, administration of triple negative breast cancer (TNBC) cells with the polypeptide APC1 increased expression of the human epidermal growth factor receptor 2 (HER2) receptor as well as the estrogen receptor on TNBC cells.

TNBC is defined inter alia by lack of expression (or at least decreased expression) of estrogen receptor (ER), progesterone receptor (PR) and human epidermal growth factor receptor 2 (HER2). In the absence of specific targets for treatment, TNBC is considered as an aggressive cancer subtype with limited treatment options. As demonstrated below, administration of APC1 increased HER2 as well as the estrogen receptor expression on the cell surface and therefore, without wishing to be bound by theory, rendered the treated cells more sensitive (or responsive) to HER2-based anti-cancer therapy.

In order to examine the combined effect of APC1 and HER2-based anti-cancer therapy on TNBC cells (that are generally regarded as insensitive to HER2-based targeted anti-cancer therapy) TNBC cells were first administered with APC1 and then for example with the specific anti-cancer agent Kadcyla, as described in the Examples below. Kadcyla is an antibody-drug conjugate (ADC) that combines the mechanisms of action of trastuzumab, an antibody directed to HER2, and the chemotherapeutic agent emtansine (DM1), in one medicine.

As demonstrated in FIG. 5A, the level of apoptosis in MDA-MB-231 cells as a result of administering Kadcyla was relatively low, as expected. Surprisingly, in cells treated with both APC1 and Kadcyla the level of apoptosis was at least 2.5 times greater than in cells treated with Kadcyla alone. In addition, expression of the HER2 receptor was also demonstrated in MDA-MB-231 tumor cells in mice treated with APC1, as shown in the Examples below.

Furthermore, as shown for example in FIG. 11B, in TNBC cells pre-treated with APC1 and then with tamoxifen, a selective estrogen-receptor modulator (SERM), cell viability decreased relative to cells treated only with tamoxifen, implying increased expression of the estrogen-receptor on the treated cells. The increase in estrogen receptor expression was directly demonstrated as well, in FIG. 13.

Surprisingly, administration of APC1 to TNBC cells (FIG. 14) as well as to mice inoculated with tumors of various cancer types (FIGS. 15, 16 and 17) resulted in reduced cell viability and reduced tumor volume, respectively, when the cells were also administered with doxorubicin or cisplatin.

Taken together the above results (which are further detailed below) demonstrate that APC1 increased the sensitivity of cancer cells to a broad spectrum of anti-cancer agents and may thus be used as an augmenter of the therapeutic effect of anti-cancer agents.

Therefore the present disclosure provides a method for treatment of cancer in a patient in need thereof, said method comprising administering to said patient an isolated polypeptide comprising the amino acid sequence denoted by SEQ ID NO: 1 or a functional fragment or derivative thereof and at least one anti-cancer agent.

By another one of its aspects the present disclosure provides an isolated polypeptide comprising the amino acid sequence denoted by SEQ ID NO: 1 or a functional fragment or derivative thereof and at least one anti-cancer agent for use in a method for treatment of cancer in a patient in need thereof.

The publication WO 2009/083968 (3) has previously shown that a polypeptide termed "KTPAF50" and fragments thereof are associated with a decrease in the viability of leukemia and prostate cancer cells and also with prevention of tumor growth in mice.

As indicated in WO 2009/083968 (3), the full length KTPAF50 polypeptide is 74 amino acid residues long and has the amino acid sequence of MPGHSRLLSIL-VSGLCVVGSSIGVLRRREQAERGSRRCAIAGEER-AMLSPSPLPE TPFSPEKGAAFSPIYPRRK (denoted herein by SEQ ID. NO: 2). Among the fragments of KTPAF50 described in WO 2009/083968 is a polypeptide lacking the N-terminal 24 amino acid residues (the signal sequence) of KTPAF50, which is denoted herein by SEQ ID NO: 3 and which has the amino acid sequence of LRR-REQAERGSRRCAIAGEERAMLSPSPLPETPFSPEK-GAAFSPIYPRRK.

The present disclosure now shows that administration of the APC peptide, having the amino acid sequence EKGAAFSPIYPRRK denoted by SEQ ID NO: 1, which consists of the 14 C-terminal amino acid residues of the peptide KTPAF50, per se to various cell types resulted in insignificant (if any) apoptosis of these cells, namely had no effect on cell viability (FIG. 5A and FIG. 5B). However, administration of APC1 with an additional anti-cancer agent (for example Kadcyla or Herceptin) resulted in apoptosis of the TNBC MDA-MB-231 cells. In other words, the responsiveness of the cells to Kadcyla was increased in the presence of the APC peptide, an effect demonstrated also in FIG. 6 and FIG. 7. The increased responsiveness was further demonstrated for Herceptin, an additional agent directed against the HER2 receptor (FIG. 9) as well as for tamoxifen (FIG. 11 and FIG. 12), doxorubicin (for example FIG. 14A) and cisplatin (for example FIG. 14B).

Therefore in some embodiments the isolated polypeptide as herein defined increases the responsiveness of said patient to said at least one anti-cancer agent.

In particular embodiments the present disclosure provides a method for treatment of cancer in a patient in need thereof, said method comprising administering to said patient an isolated polypeptide comprising the amino acid sequence denoted by SEQ ID NO: 1 or a functional fragment or derivative thereof and at least one anti-cancer agent, wherein said isolated polypeptide increases the responsiveness of said patient to said at least one anti-cancer agent.

In other embodiments the present disclosure provides an isolated polypeptide comprising the amino acid sequence denoted by SEQ ID NO: 1 or a functional fragment or derivative thereof and at least one anti-cancer agent for use in a method for treatment of cancer in a patient in need thereof, wherein said isolated polypeptide increases the responsiveness of said patient to said at least one anti-cancer agent.

In the context of the present disclosure by the term "increases responsiveness" or "increased responsiveness" it is referred to the patient's overall outcome (for example improvement) as a result of treatment, which may be assessed using any clinical parameters known to a skilled practitioner in the field of the invention. The increase in responsiveness may be evaluated by comparing the effect of a specific anti-cancer therapy on a cell sample obtained from the patient in the presence and in the absence of the isolated polypeptide as herein defined.

More specifically, the increase in responsiveness may be by at least about 1%, 2%, 3%, 4%, 5%, 6%, 7%, 8%, 9%, 10%, 110%, 12%, 13%, 14%, 15%, 16%, 17%, 18%, 19%, 20%, 21%, 22%, 23%, 24%, 25%, 26%, 27%, 28%, 29%, 30%, 31%, 32%, 33%. 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 200%, 300%, 400%, 500%, 600%, 700%, 800%, 900% or about 1000% as compared to corresponding rates in control, non-treated cells or organisms.

Assessment of responsiveness may be performed by any method known in the art, for example by assessment of tumor markers or by assessment of tumor size by computerized axial tomography (CT) or magnetic resonance imaging (MRI).

As shown below for example in FIG. 5, in the absence of APC1 the cells are less responsive to treatment by kadcyla. Therefore in some embodiments the patient as defined herein is not responsive to said anti-cancer agent when administered without said isolated polypeptide. In other words the patient as defined herein may not be responsive to said anti-cancer agent when administered alone.

In particular embodiments the present disclosure provides a method for treatment of cancer in a patient in need thereof, said method comprising administering to said patient an isolated polypeptide comprising the amino acid sequence denoted by SEQ ID NO: 1 or a functional fragment or derivative thereof and at least one anti-cancer agent, wherein said patient is not responsive to said anti-cancer agent when administered without said isolated polypeptide.

In further specific embodiments the present disclosure provides an isolated polypeptide comprising the amino acid sequence denoted by SEQ ID NO: 1 or a functional fragment or derivative thereof and at least one anti-cancer agent for use in a method for treatment of cancer in a patient in need thereof, wherein said patient is not responsive to said anti-cancer agent when administered without said isolated polypeptide.

The term "not responsive" as used herein it is meant that said patient has marginal (if any) benefit or reaction to a particular anti-cancer treatment. As indicated above responsiveness to treatment may be assessed by any method known in the art for example by assessment of tumor markers or by assessment of tumor size by computerized axial tomography (CT) or magnetic resonance imaging (MRI).

As shown herein, administration of APC1 increased the sensitivity of cancer cells to various anti-cancer agents (namely, Kadcyla, Herceptin to name but few). Without wishing to be bound by theory administration of APC1 modulated expression of cellular target(s) (termed herein "cellular moiety").

Therefore, in some embodiments the isolated polypeptide according to the present invention modulates expression of at least one cellular moiety in cancer cells in said patient. In particular embodiments the present disclosure encompasses a method for treatment of cancer in a patient in need thereof, said method comprising administering to said patient an isolated polypeptide comprising the amino acid sequence denoted by SEQ ID NO: 1 or a functional fragment or derivative thereof and at least one anti-cancer agent, wherein said isolated polypeptide modulates expression of at least one cellular moiety in cancer cells in said patient.

In further specific embodiments the invention provides an isolated polypeptide comprising the amino acid sequence denoted by SEQ ID NO: 1 or a functional fragment or derivative thereof and at least one anti-cancer agent for use in a method for treatment of cancer in a patient in need thereof, wherein said isolated polypeptide modulates expression of at least one cellular moiety in cancer cells in said patient.

By the term "modulates" as used herein it is meant to alter, increase or decrease the activity of at least one of the cellular moieties as herein defined.

By the term "cancer cells" in the context of the present disclosure it is meant to encompass any cell type and any cancer type as known in the art.

As detailed below, administration of APC1 increased HER2 expression on the cell surface as well as the expression of the estrogen receptor, and therefore without wishing to be bound by theory, renders the treated cells more sensitive (or vulnerable) to treatment targeting HER2. In addition, it is shown below that the level of glutathione in ovarian, pancreatic and TNBC cancer cells decreased upon treatment of these cells with APC1.

Therefore in some embodiments the isolated polypeptide as herein defined increases or decreases expression of at least one cellular moiety in cancer cells in said patient.

In other particular embodiments the isolated polypeptide as herein defined increases expression of at least one cellular moiety in cancer cells in said patient.

The term "cellular moiety" as herein defined encompasses any cellular molecule or fragment thereof which may be targeted by an anti-cancer agent.

By the term "increases expression" in the context of the present disclosure it is referred to escalation, rise or increment of the transcription rate, translation rate, protein and/or mRNA stability, gene product quantity and protein and/or mRNA maturation of at least one cellular moiety or fragment thereof in cancer cells in said patient. More specifically, the increase in expression may be by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 200%, 300%, 400%, 500%, 600%, 700%, 800%, 900% or about 1000% as compared to corresponding rates in control, non-treated cells or organisms.

Conversely, by the term "decreases expression" in the context of the present disclosure it is referred to decline, reduction or constriction of the transcription rate, translation rate, protein and/or mRNA stability, gene product quantity and protein and/or mRNA maturation of at least one cellular moiety or fragment thereof in cancer cells in said patient. More specifically, the decrease in expression may be by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 200%, 300%, 400%, 500%, 600%, 700%, 800%, 900% or about 1000% as compared to corresponding rates in control, non-treated cells or organisms.

The increase or decrease in expression of the cellular moiety as herein defined may be monitored by any method known in the art for example but not limited to the methods exemplified below.

As shown in the appended Examples, administration of APC1 modulated expression of cellular receptors (namely HER2 and the estrogen-receptor) as well as of glutathione. HER2 is known to be associated with control of cancer cell proliferation (growth) and metastasis (spread). As known in the art, glutathione regulates cells ability to proliferate as under stress conditions, in which reactive oxygen species (ROS) are produced in the vicinity of the tumor and glutathione inhibits the damage thereof. Furthermore, glutathione is also associated with drug resistance mechanism and may therefore inhibit the activity of chemotherapy.

Therefore in some embodiments the cellular moiety according to the present disclosure is associated with at least one of growth, regulation or spread of cancer cells. In particular, the cellular moiety according to the present disclosure is associated with an increase or a decrease in growth of cancer cells.

In some embodiments the cellular moiety as herein defined is an intra-cellular molecule moiety (namely present inside the cell) and in other embodiments a moiety present on the cell surface of said cancer cells (namely accessible on the cell surface). In still further embodiments the cellular moiety or fragment thereof is embedded in the cell membrane in a manner such that at least a fragment thereof resides inside the cell and at least another fragment thereof is present on the cell surface.

Thus in further embodiments the cellular moiety as herein defined is present on the cell surface of said cancer cells or is an intra-cellular moiety.

In further specific embodiments the cellular moiety according to the present disclosure is a receptor, a polypeptide, an enzyme, a transcription factor or an adapting molecule.

The term "receptor" as known in the art refers to a molecular structure embedded within a cell or on the surface of the cell, characterized by selective binding to a specific substance and a specific physiologic effect that results from the binding. Non-limiting examples of receptors encompassed by the present disclosure are estrogen receptor (ER), progesterone receptor (PR), human epidermal growth factor receptor 2 (HER2/neu receptor), epidermal growth factor receptor (EGFR), androgen receptor, or ST2, to name but few.

In specific embodiments the cellular moiety in accordance with the present disclosure is a cell surface receptor.

The term "cell surface receptor" (also known as "membrane receptor" or "transmembrane receptor") as referred to herein relates to a receptor embedded in the membranes of cells acting inter alia in cell signaling by binding (or interacting with) extracellular molecules. The extracellular molecules may be, among others, hormones, neurotransmitters, cytokines, growth factors, cell adhesion molecules, or nutrients, which react with the receptor to induce changes in the metabolism and activity of a cell. Non-limiting examples of cell surface receptors are the human epidermal growth factor receptor 2 (HER2/neu receptor), estrogen receptor (ER) and progesterone receptor (PR), to name but few.

In further specific embodiments the isolated polypeptide as herein defined increases expression of at least one cellular moiety in cancer cells in said patient and said cellular moiety is a receptor (for example a cell surface receptor).

In further particular embodiments, the present disclosure encompasses a method for treatment of cancer in a patient in need thereof, said method comprising administering to said patient an isolated polypeptide comprising the amino acid sequence denoted by SEQ ID NO: 1 or a functional fragment or derivative thereof and at least one anti-cancer agent, wherein said isolated polypeptide increases expression of at least one cellular moiety in cancer cells in said patient and wherein said cellular moiety is a receptor.

In still further embodiments, the present disclosure encompasses an isolated polypeptide comprising the amino acid sequence denoted by SEQ ID NO: 1 or a functional fragment or derivative thereof and at least one anti-cancer agent for use in a method for treatment of cancer in a patient in need thereof, wherein said isolated polypeptide increases expression of at least one cellular moiety in cancer cells in said patient and wherein said cellular moiety is a receptor.

In various specific embodiments the isolated polypeptide according to the present disclosure increases expression of at least one cellular moiety in cancer cells in said patient and said cellular moiety is a cell surface receptor, preferably the human epidermal growth factor receptor 2 (HER2), estrogen receptor (ER) or progesterone receptor (PR).

As detailed above, the cellular moiety as herein defined may be a receptor, a polypeptide, an enzyme, a transcription factor or an adapting molecule.

The term "polypeptide" as known in the art refers to a molecular chain of amino acid residues and the term "enzyme" as known in the art refers to a polypeptide (or protein) molecule with a characteristic sequence of amino acids that fold to produce a specific three-dimensional structure, which gives the molecule unique properties. Non-limiting examples of polypeptides encompassed by the present disclosure are programmed cell death ligand 1 (PD-L), programmed cell death ligand 2 (PD-L2) and enzyme(s) and/or polypeptide(s) associated with synthesis of glutathione.

The term "transcription factor" as herein defined refers to a molecule (or molecules) that control the rate of transcription of genetic information from DNA to messenger RNA, by binding to a specific DNA sequence.

The term "adapting molecule" as used herein refers to a molecule that can physically interact with another molecule and can change its biological activity. Non limiting examples of an adapting molecules are glutathione (GSH) having the structure (2S)-2-Amino-4-{[(R)-1-[(carboxymethyl)carbamoyl]-2-sulfanylethyl]carbamoyl}butanoic acid and molecules that contain SH2 and/or SH3 domains.

In still further embodiments the cellular moiety of the present disclosure is at least one of human epidermal growth factor receptor 2 (HER2/neu receptor), estrogen receptor (ER), progesterone receptor (PR), glutathione (GSH), epidermal growth factor receptor (EGFR), androgen receptor, B-lymphocyte antigen cluster of differentiation CD20 (CD20), cluster of differentiation 33 (CD33), programmed cell death ligand (PD-L) or ST2 receptor.

The term "Estrogen receptor" (ER) as herein defined refers to a group of proteins found inside and on surface of cells. These receptors are activated by the hormone estrogen (also termed 171-estradiol). Two classes of ER exist: nuclear estrogen receptors (ERα and ERβ), which are members of the nuclear receptor family of intracellular receptors, and membrane estrogen receptors (mERs, namely GPER (GPR30), ER-X, and Gq-mER), which are mostly G protein-coupled receptors. Once activated by estrogen, the ER is able to translocate into the nucleus and bind to DNA to regulate the activity of different genes (namely it is a DNA-binding transcription factor). ER receptors also have additional functions independent of DNA binding. The benefit of modulating cancer cells (in particular breast cancer cells) to ER positive cells is known in the art, as ER positive cells are sensitive to estrogen (and to antagonists and/or agonists thereof) and may respond to hormone therapy. A non-limiting example of therapy that may be administered to a patient diagnosed with breast cancer cells that are ER positive is tamoxifen, or any other selective estrogen-receptor modulator (SERM).

As known in the art the term "Tamoxifen" relates to an antineoplastic selective estrogen receptor modulator (SERM) hormonal therapy. Tamoxifen (2-[4-[(Z)-1,2-diphenylbut-1-enyl]phenoxy]-N,N-dimethylethanamine) acts as an anti-estrogen (inhibiting agent) in the mammary tissue, but as an estrogen (stimulating agent) in cholesterol metabolism, bone density, and cell proliferation in the endometrium. Tamoxifen competitively inhibits the binding of estradiol to estrogen receptors, thereby preventing the receptor from binding to the estrogen-response element on DNA. The result is a reduction in DNA synthesis and cellular response to estrogen. Tamoxifen is used inter alia to reduce the risk of early-stage, hormone-receptor-positive breast cancer coming back after surgery and other treatments, shrink large, hormone-receptor-positive breast cancers before surgery and treat advanced-stage, hormone-receptor-positive breast cancer, including metastatic breast cancer.

By the term "progesterone receptor" (PR, also known inter alia as NR3C3) it is referred to protein found inside cells. It is activated by the steroid hormone progesterone. In humans, PR is encoded by a single PGR gene. It has two main forms, PRA and PRB that differ in their molecular weight. A third, lesser-known isoform (PRC), also exists. Progesterone is necessary to induce the progesterone receptors. When no binding hormone is present the carboxyl terminal inhibits transcription. Binding to a hormone induces a structural change that removes the inhibitory action. Progesterone antagonists prevent the structural reconfiguration. After progesterone binds to the receptor, restructuring with dimerization follows and the complex enters the nucleus and binds to DNA. There transcription takes place, resulting in formation of messenger RNA that is translated by ribosomes to produce specific proteins.

The benefit of modulating cancer cells (in particular triple negative breast cancer cells) to PR positive cells is known in the art, as PR positive cells are sensitive to progesterone (and to antagonists and/or agonists thereof) and may respond to hormone therapy.

In particular, increasing the expression of progesterone receptors may enable targeting PR positive cells to a selective progesterone receptor modulator (SPRM), which is an agent that acts on the progesterone receptor. SPRMs can be distinguished from full receptor agonists (such as progesterone) and full antagonists (such as aglepristone) since their action differs in different tissues, i.e. they act as an agonist in some tissues while antagonist in others. This mixed profile of action leads to stimulation or inhibition in a tissue-specific manner.

As indicated above increased expression of HER2 was demonstrated in the presence of APC1 in cells regarded as TNBC and therefore the present disclosure relates inter alia to administration a combination of APC1 (denoted by SEQ ID NO: 1) and an anti-cancer agent directed to HER2 (e.g. Kadcyla or Herceptin) for the treatment of triple negative breast cancer.

"Human epidermal growth factor receptor 2" (also known as NEU. NGL. HER2, TKR1, HER-2, c-erb B2 and HER-2/neu), as known in the art is encoded by the human epidermal growth factor receptor 2 gene (ERBB2) that is amplified in approximately 18% to 20% of breast cancers. Amplification is the primary mechanism of HER2 overexpression and abnormally high levels of a 185-kd glycoprotein with tyrosine kinase activity are found in these tumors. HER2 overexpression is associated with clinical outcomes in patients with breast cancer. There are several possible uses of HER2 status, inter alia assessing prognosis and predicting the responsiveness for several systemic therapies. Thus, HER2 status might be incorporated into a clinical decision (with other prognostic factors) of the type of the recommended anti-cancer therapy. Importantly, several studies have shown that agents that target HER2 are remarkably effective in both the metastatic and adjuvant settings. For example Trastuzumab (Herceptin), a humanized monoclonal antibody, improves response rates, time to progression, and even survival when used alone or added to chemotherapy in metastatic breast cancer in HER2 positive patients.

As known in the art by the term "glutathione" (GSH. Glutathione (γ-L-Glutamyl-L-cysteinylglycine) it is referred to a small amino acid containing molecule (peptide) comprising L-glutamic acid, L-cysteine, and Glycine. The molecule is found in the food supply and in the human body where it acts as an antioxidant. The 'glutathione system' comprises enzymes that synthesize glutathione within the cell and enzymes that use glutathione as the means to exert antioxidant effects. Glutathione is also associated with multi-drug resistance. It has been previously shown that resistance and cross-resistance between alkylating agents, radiation therapy and cisplatin is associated with elevations in cellular GSH levels.

By the term "epidermal growth factor receptor" (EGFR, ErbB1 or HER1) as known in the art and as used herein it is referred to a member of the epidermal growth factor family of receptor tyrosine kinases (ErbBs) which plays essential roles in regulating cell proliferation, survival, differentiation and migration. Loss of regulation of the ErbB receptors underlies many human diseases, most notably cancer. EGFR is a single chain transmembrane glycoproteins consisting of an extracellular ligand-binding ectodomain, a transmembrane domain, a short juxtamembrane section, a tyrosine kinase domain and a tyrosine-containing C-terminal tail. Binding of soluble ligand to the ectodomain of the receptor promotes homo- and heterodimer formation between receptors. Receptor dimerization is essential for activation of the intracellular tyrosine kinase domain and phosphorylation of the C-terminal tail. Phosphotyrosine residues then activate, either directly or through adaptor proteins, downstream components of signaling pathways. EGFR is a target for rational design of targeted anti-cancer agents. Anti-cancer agents targeting EGFR are well known in the art and include inter alia Erlotinib hydrochloride (Tarceva), lapatinib (Tykerb), Cetuximab (Erbitux), Panitumumab (Vectibix) or Gefitinib (Iressa).

The term "androgen receptor" as known in the art refers to a protein having 3 major functional domains, the N-terminal domain, the DNA-binding domain, and an androgen-binding domain. The protein functions as a steroid-hormone activated transcription factor. Upon binding the hormone ligand, the receptor dissociates from accessory proteins, translocates into the nucleus, dimerizes, and then stimulates transcription of androgen responsive genes. The androgen receptor has been implicated with various cancers, among which are prostate and breast cancer. Targeting androgen receptor by specific agents is well known in the art.

"B-lymphocyte antigen cluster of differentiation CD20" (CD20) as known in the art and used herein refers to an activated-glycosylated phosphoprotein expressed on the surface of all B-cells. The B-lymphocyte surface molecule plays a role in the development and differentiation of B-cells into plasma cells. CD20 is the target of various monoclonal antibodies, inter aha rituximab, obinutuzumab. Ibritumoma tiuxetan, and tositumomab, which are all active agents in the treatment of all B cell lymphomas and leukemias.

By the term "Cluster of differentiation 33" (CD33) as known in the art and used herein it is referred to a transmembrane receptor expressed on cells of myeloid lineage. It is usually considered myeloid-specific, but it can also be found on some lymphoid cells. It binds sialic acids, therefore is a member of the SIGLEC family of lectins.

The term "programmed cell death ligand (PD-L)" refers to a ligand of a programmed cell death receptor, as known in the art. Non limiting examples for programmed cell death ligands are PD-L and PD-L2.

The term "ST2 receptor" or T1/ST2 receptor (also referred to as "T1/ST2" and "ST2/T1") as herein defined refers to a member of the IL-IR superfamily, which possesses three extracellular immunoglobulin domains and an intracellular TIR domain.

It should be appreciated that modulating the expression of any cellular moiety or fragment thereof as herein defined by administration of the isolated polypeptide of the invention expands anti-cancer treatment options to a patient in need thereof via altering the responsiveness of the cells to various anti-cancer agents.

According to the American Cancer Society, until the late 1990s cancer therapy consisted of cytotoxic agents (chemotherapy drugs) which act by killing proliferating cells, with the exception of hormone treatments. These agent also affect normal cells, but to a lesser extent. In contrast to traditional chemotherapy drugs, targeted therapies act by influencing the processes in control of growth, division, and spread of cancer cells, as well as the signals that cause cancer cells to die naturally. Targeted therapies work in various pathways.

The term "anti-cancer agent" is used herein at its broadest sense and refers to any anticancer or antineoplastic drug known in the art used to treat cancer and control the growth of cancerous cells. In various embodiments the anti-cancer agent is an anti-cancer agent targeting a cellular moiety or fragment thereof and refers to a drug (a molecule) that blocks the growth and/or spread of cancer by interacting with at least one specific molecule or moiety (also referred to as "molecular targets") involved in the growth, progression, and spread of cancer. Targeted cancer therapies are sometimes called "molecularly targeted drugs". "molecularly targeted therapies" or "precision medicines".

In some embodiments the anti-cancer agent of the present disclosure is a targeted therapy, namely an anti-cancer agent targeting a cellular molecule, moiety or fragment thereof that resides inside the cell or on its surface (at least partially).

Targeted therapies differ from standard chemotherapy by acting on specific molecular targets (or "cellular moiety" as defined herein) that are associated with cancer, whereas most standard chemotherapies act on all rapidly dividing normal and cancerous cells.

As demonstrated in the Examples herein, administration of TNBC cells with the polypeptide APC1 increased expression of the human epidermal growth factor receptor 2 (HER2) receptor and of the estrogen receptor alpha in TNBC cells, rendering these cells more sensitive to HER2 or ER based anti-cancer therapy.

Therefore in some embodiments said at least one anti-cancer agent according to the present disclosure directly or indirectly interacts with said at least one cellular moiety.

In particulars embodiments the present disclosure provides a method for treatment of cancer in a patient in need thereof, said method comprising administering to said patient an isolated polypeptide comprising the amino acid sequence denoted by SEQ ID NO: 1 or a functional fragment or derivative thereof and at least one anti-cancer agent, wherein said isolated polypeptide increases or decreases expression of at least one cellular moiety in cancer cells in said patient and wherein said at least one anti-cancer agent directly or indirectly interacts with said at least one cellular moiety.

In other embodiments the present disclosure provides an isolated polypeptide comprising the amino acid sequence denoted by SEQ ID NO: 1 or a functional fragment or derivative thereof and at least one anti-cancer agent for use in a method for treatment of cancer in a patient in need thereof, wherein said isolated polypeptide increases or decreases expression of at least one cellular moiety in cancer cells in said patient and wherein said at least one anti-cancer agent directly or indirectly interacts with said at least one cellular moiety.

The term "interacts with" as used herein in the context of the anti-cancer agent, means to connect or contact with a target either directly or indirectly so as to alter the activity of the target (cellular moiety), including, by way of example only, to enhance the activity of the target, to inhibit the activity of the target, to limit the activity of the target, or to extend the activity of the target.

There are various types of targeted cancer therapies, for example growth signal inhibitors, angiogenesis inhibitors and apoptosis-inducing drugs, to name but few. In some embodiments of the method and other aspects of the present disclosure the at least one anti-cancer agent directly or indirectly inhibits at least one of growth or spread of cancer cells in said patient.

In specific embodiments the at least one anti-cancer agent as herein defined directly or indirectly inhibits at least one of growth or spread of cancer cells in said patient.

The term "growth" as used herein refers to the increase in cytoplasmic volume, cell development and cell reproduction as well as to the increase in size or population of cells. The term "spread" in the context of cancer cells relates to cancer cell metastasis and the various cellular processes enabling or resulting in metastasis. By the term "inhibits" or "inhibition" as referred to herein, it is related to the retardation or reduction of at least one of growth or spread of cancer cells by any one of about 1% to 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

In further specific embodiments the at least one anti-cancer agent as herein defined directly or indirectly interacts with said at least one cellular moiety, wherein said cellular moiety is a cell surface receptor.

In particular the present disclosure encompasses a method for treatment of cancer in a patient in need thereof, said method comprising administering to said patient an isolated polypeptide comprising the amino acid sequence denoted by SEQ ID NO: 1 or a functional fragment or derivative thereof and at least one anti-cancer agent, wherein said isolated polypeptide increases expression of at least one cell surface receptor in cells of said patient and wherein said at least one anti-cancer agent directly or indirectly interacts with said at least one cell surface receptor.

In further embodiments the present disclosure encompasses an isolated polypeptide comprising the amino acid sequence denoted by SEQ ID NO: 1 or a functional fragment or derivative thereof and at least one anti-cancer agent for use in a method for treatment of cancer in a patient in need thereof, wherein said isolated polypeptide increases expression of at least one cell surface receptor in cells of said patient and wherein said at least one anti-cancer agent directly or indirectly interacts with said at least one cell surface receptor.

In various embodiments the anti-cancer agent according to the present disclosure is an immunotherapy, a chemotherapeutic agent, a signal transduction inhibitor, a receptor inhibitor, a gene expression modulator, an apoptosis inducer, an angiogenesis inhibitor, a hormone therapy, a metabolic inhibitor, an anti-autophagy agent (e.g. Bleomycin or Doxorubicin), an endoplasmic reticulum stress inducer, a reactive oxygen species (ROS) inducer or a combination thereof.

As exemplified below, the effect of various immunotherapy anti-cancer agents was shown to be enhanced or augmented in upon administration of the peptide APC1, for example antibodies directed against the human epidermal growth factor receptor 2 (HER2/neu receptor).

As known in the art, by the term "immunotherapy" (also referred to as "biologic therapy" or "biotherapy") in the context of cancer therapy it is referred to treatment that triggers the immune system to destroy cancer cells. Currently the main types of immunotherapy used to treat cancer include, inter alia, monoclonal antibodies, cancer vaccines and immune checkpoint inhibitors. These proteins help keep immune responses in check and can keep T cells from killing cancer cells. When these proteins are blocked, the so-called "brakes" on the immune system are released and T cells are able to kill cancer cells better. Examples of checkpoint proteins found on T cells or cancer cells include PD-1/PD-L1 and CTLA-4/B7-1/B7-2.

Other immunotherapies include monoclonal antibodies that recognize specific molecules on the surface of cancer cells, wherein binding of the monoclonal antibody to the target molecule results in the immune destruction of cells expressing that target molecule (herein referred to as "cellular moiety", for example a cell surface receptor).

Therefore in various specific embodiments the anti-cancer agent of the present disclosure is an immunotherapy, for example an antibody, a monoclonal antibody or any fragment or conjugate thereof.

In other embodiments the anti-cancer agent according to the present disclosure is an immunotherapy, preferably a monoclonal antibody or a conjugated antibody. In various further embodiments the monoclonal antibody or a conjugated antibody as herein defined is directed against at least one of epidermal growth factor receptor 2 (HER2), estrogen receptor (ER) or progesterone receptor (PR). In specific embodiments the at least one anti-cancer agent according to the present disclosure is directed to Her2/neu receptor. In still further embodiments the monoclonal antibody is directed against PD-L1.

The term "antibody" is used herein in its broadest sense and refers to a polypeptide encoded by an immunoglobulin gene or functional fragments thereof that specifically bind and recognize an antigen and includes monoclonal antibodies, polyclonal antibodies, monovalent antibodies, multivalent antibodies, multi-specific antibodies (e.g. bispecific antibodies) and also includes antigen-binding antibody fragments. Such antigen-binding fragments may be for example Fab and F(ab')$_2$, which are capable of binding antigen. Such fragments may be produced by any method known in the art, for example by proteolytic cleavage, using enzymes such as papain (to produce Fab fragments) or pepsin (to produce F(ab')$_2$ fragments). An antibody can be chimeric, human, humanized and/or affinity matured.

The term "monoclonal antibody" (mAb) as herein defined refers to a population of substantially homogenous antibodies, i.e., the individual antibodies comprising the population are identical except for possibly naturally occurring mutations that may be present in minor amounts. Monoclonal antibodies are directed against a single antigenic site (epitope).

Monoclonal antibodies may be prepared and purified by any method known in the art. For example, monoclonal antibodies may be prepared from B cells taken from the spleen or lymph nodes of immunized animals (e.g. rats, mice or monkeys), by fusion with immortalized B cells under conditions which favor the growth of hybrid cells.

The term "conjugated antibody" (also known as an "immunoconjugate") as herein defined refers to an antibody or any antigen-binding fragment thereof according to the invention that is conjugated (linked or joined) to an additional agent. Immunoconjugates may be prepared by any method known to a person skilled in the art, for example, by cross-linking the additional agent to the antibody according to the invention or by recombinant DNA methods.

Preparation of antibodies is well known in the art. In various specific embodiments a monoclonal antibody delivers toxic molecules that can cause the death of cancer cells, specifically the conjugated antibody Kadcyla. Kadcyla, also known as Trastuzumab emtansine or ado-trastuzumab emtansine is an antibody-drug conjugate consisting of the monoclonal antibody trastuzumab (also known as Herceptin) linked to the cytotoxic agent emtansine (DM1). Trastuzumab alone stops growth of cancer cells by binding to the HER2/neu receptor, whereas DM1 enters cells and destroys them by binding to tubulin. Trastuzumab binding to Her2 prevents homodimerization or heterodimerization (Her2/Her3) of the receptor, ultimately inhibiting the activation of MAPK and PI3K/Akt cellular signalling pathways. Because the monoclonal antibody targets HER2, and HER2 is only over-expressed in specific cancer cells, the conjugate delivers the toxin specifically to tumor cells.

Therefore in still further specific embodiments the anti-cancer agent as herein defined is a monoclonal antibody or a conjugated antibody directed against HER2. In additional embodiments the at least one anti-cancer agent as herein defined is Kadcyla or Herceptin.

By the term "signal transduction inhibitor" it is referred to a substance that blocks signals passed from one molecule to another. Blocking these signals can affect many cellular functions, including cell division and cell death, and thereby may kill cancer cells. In other words, signal transduction inhibitors block the activities of molecules participating in signal transduction, the process by which a cell responds to signals from its environment. In some cancers, malignant cells are stimulated to divide continuously without being prompted to do so by external growth factors. Signal transduction inhibitors interfere with this inappropriate signaling.

By the term "receptor inhibitor" as known in the art it is meant any substance that blocks or at least modulates the activity of a receptor. In some non-limiting embodiments a receptor inhibitor refers to an inhibitor of a member of the epidermal growth factor receptor family, namely a substance that blocks the activity of a member of the epidermal growth factor receptor (EGFR) family. Epidermal growth factor receptors are found on the surface of some normal cells and are involved in cell growth. EGFRs may also be found at high levels on some types of cancer cells, which causes these cells to grow and divide, where blocking EGFRs may inhibit cancer cells growth.

Some non-limiting receptors encompassed by the present disclosure are human epidermal growth factor receptor 2 (HER2/neu receptor), estrogen receptor (ER), progesterone receptor (PR), epidermal growth factor receptor (EGFR), androgen receptor, CD20, or ST2 to name but few.

In various additional embodiments the anti-cancer agent as herein defined acts by blocking the estrogen receptor (e.g. Tamoxifen, Fulvestrant).

In specific embodiments the at least one anti-cancer agent according to the present disclosure directly or indirectly interacts with said at least one cellular moiety, wherein said at least one cellular moiety is a cell surface receptor, for example HER2, ER and/or PR. In other embodiments the anti-cancer agent according to the present disclosure is directed to HER2, ER and/or PR. In still further specific embodiments the anti-cancer agent according to the present disclosure is a receptor inhibitor, preferably an inhibitor of epidermal growth factor receptor (EGFR).

The term "gene expression modulator" as herein defined refers to agents that are associated with controlling gene expression directly or indirectly.

By the term "apoptosis inducer" as used herein it is meant an agent that causes cancer cells to undergo a process of controlled cell death, namely apoptosis. Some non-limiting examples of apoptosis inducers include Doxorubicin, bleomycin, cis-Platin. Fluorouracil (5FU), to name but few.

Doxorubicin (also referred to e.g. as Adriamycin or Doxil) having the structure (7S,9S)-7-[(2R,4S,5S,6S)-4-amino-5-hydroxy-6-methyloxan-2-yl]oxy-6,9,11-trihydroxy-9-(2-hydroxyacetyl)-4-methoxy-8,10-dihydro-7H-tetracene-5,12-dione is an antineoplastic antibiotic obtained from *Streptomyces peucetius*. Doxorubicin is an Anthracycline Topoisomerase Inhibitor that intercalates between base pairs in the DNA helix, thereby preventing DNA replication and ultimately inhibiting protein synthesis. Additionally, doxorubicin inhibits topoisomerase II which results in an increased and stabilized cleavable enzyme-DNA linked complex during DNA replication and subsequently prevents the ligation of the nucleotide strand after double-strand breakage. Doxorubicin also forms oxygen free radicals (ROS) resulting in cytotoxicity secondary to lipid peroxidation of cell membrane lipids. Any derivatives of doxorubicin are encompassed by the present disclosure.

Cisplatin, cisplatinum or cis-diamminedichloroplatinum (II) ($Cl_2H_6N_2Pt$) is a platinum-based chemotherapy drug used to treat various types of cancers, it was the first member of its class, which now also includes carboplatin and oxaliplatin.

In specific embodiments the present disclosure provides a method for treatment of cancer in a patient in need thereof, said method comprising administering to said patient an isolated polypeptide comprising the amino acid sequence denoted by SEQ ID NO: 1 or a functional fragment or derivative thereof and at least one anti-cancer agent, wherein said at least one anti-cancer agent is an apoptosis inducer, preferably doxorubicin, doxorubicin derivative or cisplatin.

In further embodiments the present disclosure provides an isolated polypeptide comprising the amino acid sequence denoted by SEQ ID NO: 1 or a functional fragment or derivative thereof and at least one anti-cancer agent for use in a method for treatment of cancer in a patient in need thereof, wherein said at least one anti-cancer agent is an apoptosis inducer, preferably doxorubicin, doxorubicin derivative or cisplatin.

The term "an angiogenesis inhibitor" as used herein refers to an agent that blocks the growth of new blood vessels to tumors (tumor angiogenesis). Some targeted therapies that inhibit angiogenesis interfere with the action of the vascular endothelial growth factor (VEGF), a substance that stimulates new blood vessel formation.

The term "hormone therapy" as known in the art and used herein refers to an agent that stops or at least slows growth of hormone-sensitive tumors, which require certain hormones to grow. Hormone therapies act by preventing the body from producing the hormones or by interfering with the action of hormones. Examples of hormone therapies include but are not limited to tamoxifen, raloxifene, Aromatase inhibitors and Luteinising hormone (LH) blockers for the treatment and prevention of breast cancer and Luteinizing hormone-releasing hormone (LHRH) agonists for the treatment of prostate cancer.

A "metabolic inhibitor" as used herein refers to an agent that interferes with cancer cell metabolism, for example an agent that inhibits glycolysis (e.g. Daunorubicin (also known as daunomycin) or Paclitaxel), an agent that inhibits mitochondria metabolism (e.g. Paclitaxel or Omeprazole), to name but few.

As detailed in the Examples below, the sensitivity of cancer cells to doxorubicin or cisplatin increased upon pre-administration with APC1. Doxorubicin and cisplatin may be classified inter alia as chemotherapeutic agents.

As well known in the art a "chemotherapeutic agent" is used for treatment of cancer, sometimes in combination with other agents over a period of days to weeks. Such agents are toxic to cells with high proliferative rates.

Therefore by further embodiments the at least one anti-cancer agent as herein defined is a chemotherapeutic agent, preferably doxorubicin or doxorubicin derivative, cisplatin, taxol or a reactive oxygen species (ROS) inducer.

By the term "anti-autophagy agent" as herein defined it is meant to include any agent that inhibits, at least partially, any of the processes involved in autophagy. As known in the art autophagy is a process that facilitates nutrient recycling via degradation of damaged organelles and proteins and is accepted as a cyto-protective mechanism against at least neurodegenerative diseases. However, autophagy inhibition is desired in the treatment of various cancers (e.g. with Chloroquine or Hydroxychloroquine in combination with other drugs for the treatment of multiple neoplasms).

By the term "endoplasmic reticulum stress inducer" as herein defined it is meant to include any agent that enhances or stimulates stress in the endoplasmic reticulum (ER). As known in the art, the endoplasmic reticulum (ER) functions to properly fold and process secreted and transmembrane proteins. Agents that disrupt ER function cause an accumulation of misfolded and unfolded proteins in the ER lumen, a condition known as "ER stress". Under unresolvable ER stress conditions, apoptosis is promoted as desired in the treatment of various cancer types.

Reactive oxygen species (ROS), a group of ions and molecules, include hydroxyl radicals ($\cdot OH$), alkoxyl radicals, superoxide anion ($O_2 \cdot -$), singlet oxygen and hydrogen peroxide ($H_2O_2$) all of which are highly reactive chemical species. Endogenous ROS are mostly formed in mitochondria during respiration. While low levels of ROS play important roles in regulating biological functions in mammalian cells, excess production of ROS can induce cell death by oxidative damaging effects to intracellular bio-macromolecules. Induction of cell death is desired in treatment of various cancer types and therefore ROS play an important role as anti-tumor therapy.

Indeed, some anticancer drugs, such as molecular targeted drugs and chemotherapeutic agents, effectively kill cancer cells by inducing ROS generation. In addition, photodynamic therapy (PDT) is mainly based on induction of ROS burst to kill cancer cells. The mechanism of cell death induced by radiotherapy using ionizing radiation also refers to ROS production. Therefore the term "reactive oxygen species (ROS) inducer" as used herein refers to any agent that induces production of ROS.

As indicated above the isolated polypeptide as herein defined is administered with at least one anti-cancer agent. By the term "at least one" it is meant to include one, two, three, four, five, six, seven, eight, nine, ten or more anti-cancer agent(s) as herein defined.

As indicated above the present invention is based on the finding that administration of cells with the isolated polypeptide of the present disclosure increased expression of the human epidermal growth factor receptor 2 (HER2) receptor on the cell surface of TNBC cells, rendering these cells prone to targeted therapy directed to the HER2 receptor. Indeed, in cells treated with both the peptide APC1 and Kadcyla the level of apoptosis was at least 2.5 times greater than in cells treated with Kadcyla alone. The appended Examples also demonstrate that the peptide of the present disclosure enhanced the estrogen receptor expression and the effect of tamoxifen (e.g. FIG. 11. FIG. 12 and FIG. 13) and of other anti-cancer agents, namely doxorubicin and cisplatin (FIG. 14, FIG. 15, FIG. 16 and FIG. 17).

The present disclosure therefore provides a combination therapy, in which the isolated polypeptide of the invention is administered with at least one anti-cancer agent. In other words the present disclosure provides a method for treatment of cancer in a patient in need thereof, comprising administering to said patient an isolated polypeptide comprising the amino acid sequence denoted by SEQ ID NO: 1 or a functional fragment or derivative thereof in combination with at least one anti-cancer agent.

The present invention further provides an isolated polypeptide comprising the amino acid sequence denoted by SEQ ID NO: 1 or a functional fragment or derivative thereof in combination with at least one anti-cancer agent for use in a method for treatment of cancer in a patient in need thereof.

The term "combination" or "combination therapy" can mean concurrent or consecutive administration of two or more agents (namely of the isolated polypeptide as herein defined and the at least one anti-cancer agent). For example, concurrent (simultaneous) administration means that the two or more agents are administered in parallel (at the same time) whereas consecutive administration means that the two or more agents are administered to the patient at different times and optionally by different routes of administration.

In specific embodiments the combination as herein defined increases the responsiveness of said patient to said at least one anti-cancer agent by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 290%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 200%, 300%, 400%, 500%, 600%, 700%, 800%, 900% or about 1000% as compared to corresponding rates in cells or organisms that were treated only with said at least one anti-cancer agent.

In various embodiments the isolated polypeptide according to the present disclosure is administered prior to, concomitantly with or after the administration of said at least one an anti-cancer agent. Administration of the isolated polypeptide and the at least one anti-cancer agent as herein defined may be performed by any route known in the art.

Administration according to the present invention may be performed by any of the following routes: oral administration, intravenous, intramuscular, intraperitoneal, intratechal or subcutaneous injection, intrarectal administration, intranasal administration, ocular administration or topical administration.

In particular embodiments the isolated polypeptide as herein defined is administered prior to administration of said at least one an anti-cancer agent. In further specific embodiments the isolated polypeptide as herein defined is administered about 1-7 days prior to administration of said at least one anti-cancer agent.

As detailed above the present invention provides a method and an isolated polypeptide for use in the treatment of cancer.

As used herein the terms "cancer" and "tumor" are used in their broadest sense and relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the methods and additional aspects of the present invention may be used in the treatment of non-solid and solid tumors. Diagnosis of cancer and of cancer type is performed by a skilled physician as well known in the art.

Non-limiting examples of cancer types include adrenocortical cancer, melanoma, Malignant melanoma, Non-melanoma skin cancer. Kaposi's Sarcoma, Bladder cancer, Colon cancer, Colorectal cancer, Rectal cancer, Neuroectodermal and Pineal cancer, Childhood Brain Stem Glioma, Childhood Cerebellar Astrocytoma. Childhood Cerebral Astrocytoma, Childhood medulloblastoma, Childhood visual pathway Glioma, Meningioma, Mixed Glioma, Oligodendroglioma, Astrocytoma, Ependymoma, Pituitary adenoma. Metastasic Adenocarcinoma. Acoustic neuroma, Paravertebral Malignant teratoma, Breast cancer, Ductal carcinoma. Mammary gland neoplasia, Ovarian cancer, Carcinoid tumor, Cervical cancer, Uterus cancer, Endometrial cancer, Vaginal cancer, vulva cancer, Gestational Trophoblastic cancer, Fallopain cancer, Uterine sarcoma, Cutaneous T-cell Lymphoma, Lymphoma (Hodgkin's disease and Non-Hodgkin's disease), Retinoblastoma, Soft tissue Sarcomas, Wilm's tumor, Fanconi Anaemia, Langerhan's Cells Histiocytosis, Malignant Rhabdoid Tumour of Kidney, Liver cancer, Neuroblastoma, Retinoblastoma, Choriocarcinoma, Endocrine cancers, Esophageal cancer, Ewing's Sarcoma, Eye cancer, Gastric cancer, Gastrointestinal cancers, Genitourinary cancers, Glioma, Gynaecological cancers, Head and neck cancer, Hepatocellular cancer, Hypopharynx cancer, Islet call cancer, Kidney cancer, Laryngeal cancer, Lung cancer, Male breast cancer, Mesothelioma, Myeloma multiple. Nasopharyngeal cancer, Non-melanoma Skin cancer, Oesophageal cancer. Ostcosarcoma, Pancreas cancer, Pituitary cancer, Prostate cancer, Renal cell carcinoma Retinoblastoma, Rhabdomyosarcoma, Sarcoma, Skin cancer, Squamous cell carcinoma, Stomach cancer, Testicular cancerthymus cancer, Thyroid cancer, Transitional cells cancer, Trophoblastic cancer, Acute Lymphatic leukemia. Leukemia, Acute myeloid leukemia. Adenocystic carcinoma, Anal cancer, Bone cancer, Bowel cancer, Liposarcoma, Nephroblastoma and Osteosarcoma.

Specific cancer types encompassed by the present disclosure are cancer types which will benefit from increased responsiveness to said at least one anti-cancer agent, for example as manifested by an increase in the expression level of at least one cellular moiety (e.g. a receptor, a cell surface receptor to name but few) by administration of the isolated polypeptide as herein defined.

In further specific embodiments cancer according to the present disclosure is at least one of breast cancer, ovarian cancer, prostate cancer, lung cancer, colon cancer. B cell lymphoma, Acute Myeloid Leukemia (AML) or pancreatic cancer.

As demonstrated below the isolated peptide APC1 administered to MDA231, MDA-MB-468 and BTS49 (all of which are triple negative breast cancer cell lines) increased the sensitivity of these cells to treatment with an anti-cancer agent that specifically targets a molecular moiety, the receptor HER2. Therefore in specific embodiments cancer as herein defined is breast cancer. In further specific embodiments cancer as herein defined is triple negative breast cancer (TNBC).

The term "Triple-negative breast cancer" (TNBC) refers to any breast cancer that does not express the genes for estrogen receptor (ER), progesterone receptor (PR) or Her2/neu. Lack of expression of the above receptors render TNBC more difficult to treat as most chemotherapies target one of the three receptors.

As known in the art, certain breast cancer treatment strategies, like hormonal therapy (e.g. anti-estrogens) or targeted therapy (e.g. trastuzumab), are only effective when corresponding receptors and targets are expressed by tumor cells. In breast cancer, a hormonal therapy requires estrogen (ER) and/or progesterone receptor (PR) expression to be effective, while trastuzumab therapy applies only to tumors harboring overexpression of HER2 due to amplification of its encoding oncogene ERBB2. As indicated above, targeted therapy (e.g. hormonal therapy and trastuzumab) cause less adverse side effects than chemotherapy and has additional advantages over chemotherapy (e.g. prolong disease-free survival and overall survival of the patient). However, some cancer tumors neither express ER and PR, nor do they overexpress HER2 (e.g. TNBC).

Triple-negative breast cancers comprise a heterogeneous group of cancers. Any type of TNBC is encompassed by the present disclosure. In the above and other embodiments TNBC is advanced TNBC, locally advanced TNBC or metastatic TNBC.

By another one of its aspects the present disclosure provides a method for treatment of triple negative breast cancer (TNBC) in a patient in need thereof, said method comprising administering to said patient an isolated polypeptide comprising the amino acid sequence denoted by SEQ ID NO: 1 or a functional fragment or derivative thereof and at least one anti-cancer agent.

The present disclosure further provides a an isolated polypeptide comprising the amino acid sequence denoted by SEQ ID NO: 1 or a functional fragment or derivative thereof and at least one anti-cancer agent for use in a method for treatment of triple negative breast cancer (TNBC) in a patient in need thereof.

In further specific embodiments said at least one anti-cancer agent as herein defined is directed to HER2, ER and/or PR.

In various specific embodiments the isolated polypeptide as herein defined increases expression of at least one of human epidermal growth factor receptor 2 (HER2/neu receptor), estrogen receptor (ER) or progesterone receptor (PR) in cancer cells in said patient.

In further specific embodiments the anti-cancer agent according to the present disclosure interacts with Her2/neu receptor (e.g. the anti-cancer agent as herein defined is an antibody directed against the Her2/neu receptor, such as Kadcyla or Herceptin), ER (e.g. the anti-cancer agent as herein defined is tamoxifen or raloxifene) or PR.

In further embodiments the at least one anti-cancer agent according to the present disclosure is a chemotherapeutic agent, preferably doxorubicin or doxorubicin derivative, cisplatin, taxol or a reactive oxygen species (ROS) inducer.

The terms "treat", "treating", "treatment" as used herein mean ameliorating one or more clinical indicia of disease activity in a patient as herein defined. "Treatment" refers to therapeutic treatment. Those in need of treatment are mammalian subjects suffering from cancer. Thus by the term "patient" or "patient in need thereof" it is meant any mammal, for example human, for which administration of the isolated polypeptide as herein defined and at least one anti-cancer agent, or any pharmaceutical composition of same, is desired in order to overcome or at least slow down cancer, in particular human patients. Cancer diagnosis may be performed by any method known to a skilled physician.

In some embodiments a patient in need thereof according to the invention is a subject diagnosed as inflicted with breast cancer and in particular embodiments a patient in need thereof refers to a subject diagnosed as inflicted with triple-negative breast cancer (TNBC).

In various embodiments the patient in need thereof as herein defined has been previously administered with chemotherapy and experienced cancer progression or relapse.

The present disclosure further provides the use of an isolated polypeptide comprising the amino acid sequence denoted by SEQ ID NO: 1 or a functional fragment or derivative thereof and at least one anti-cancer agent in the preparation of medicament(s) for the treatment of cancer or for the treatment of triple negative breast cancer (TNBC) in a patient in need thereof.

As indicated above the present disclosure provides a method for treatment of cancer in a patient in need thereof, said method comprising administering to said patient an isolated polypeptide comprising the amino acid sequence denoted by SEQ ID NO: 1 or a functional fragment or derivative thereof and at least one anti-cancer agent.

As detailed herein below, the present disclosure exemplifies increased responsiveness of cancer cells to treatment with an anti-cancer agent upon administration of cancer cells (or animals, as the case may be) with the peptide APC1 having the amino acid sequence EKGAAFSPIYPRRK as denoted by SEQ ID NO: 1.

The term "isolated polypeptide" as herein defined encompasses a polypeptide comprising the amino acid sequence denoted by SEQ ID NO. 1 (termed herein "APC1") or a functional fragment or derivative of the amino acid sequence denoted by SEQ ID NO. 1 or pharmaceutically acceptable salts of said isolated peptide. The term "isolated" refers to molecules, such as the amino acid sequences described herein, peptides or polypeptides that are removed from their natural environment, isolated or separated.

In specific embodiments the isolated polypeptide according to the present disclosure consists of the amino acid sequence denoted by SEQ ID NO: 1. In other embodiments the isolated polypeptide according to the present disclosure consists of the amino acid sequence denoted by SEQ ID NO: 2 or by SEQ ID NO: 3.

As indicated above, a "polypeptide" refers to a molecular chain of amino acid residues, which can be optionally modified at one or more of its amino acid residues, for example by manosylation, glycosylation, amidation (for example C-terminal amides), carboxylation or phosphorylation. The polypeptide of the present disclosure may be obtained synthetically, through genetic engineering methods, expression in a host cell, or through any other suitable means as known in the art. Methods for producing peptides or polypeptides are well known in the art.

The term "amino acid" as used herein, refers to naturally occurring and synthetic amino acid residues, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. The term amino acid encompasses L-amino acids and D-amino acids, which are mirror images of L-amino acids, where the chirality at carbon alpha has been inverted.

The terms "amino acid sequence" or "polypeptide sequence" also relate to the order in which amino acid residues, connected by peptide bonds, lie in the chain in peptides and proteins. The sequence is generally reported from the N-terminal end containing free amino group to the C-terminal end containing free carboxyl group.

By the term "comprising" it is meant that the isolated polypeptide in accordance with the present disclosure includes the amino acid sequence denoted by SEQ ID NO: 1, but may also include additional amino acid residues at the N-terminus or at the C-terminus of the peptide or at both termini (for example the isolated polypeptide may comprise the amino acid sequence denoted by SEQ ID NO: 1 such that it consists of the amino acid sequence denoted by SEQ ID NO: 2 or SEQ ID NO: 3, both comprising the amino acid sequence denoted by SEQ ID NO: 1 at their C termini). The isolated polypeptide encompassed by the present disclosure also includes a polypeptide comprising the amino acid sequence denoted by SEQ ID NO: 1 in which the N-terminus and/or the C-terminus of the peptide denoted by SEQ ID NO: 1 carries a protecting group. Protective (or protecting) groups are well known in the art and include inter alia alcohol protecting groups, amine protecting groups, carbonyl protecting groups and others.

As indicated above, the present disclosure also encompasses isolated polypeptides comprising a functional fragment or derivative of the polypeptide having the amino acid sequence denoted by SEQ ID NO. 1.

The term "fragment" as herein defined refers to any peptide or polypeptide which is at least one amino acid shorter than the isolated polypeptide in accordance with the present disclosure, obtained by deletion of at least one amino acid residue from the polypeptide in accordance with the invention.

Specifically, a fragment of the isolated polypeptide in accordance with the invention is a polypeptide that comprises a contiguous amino acid portion of SEQ ID NO: 1 that is 1, 2, 3, 4, 5 or more amino acid residues shorter than the sequence denoted by SEQ ID NO: 1. In other words, the fragment as herein defined may include 9, 10, 11, 12, 13 or 14 amino acid residues of the sequence denoted by SEQ ID NO: 1.

By the term "derivative" or "derivatives" it is meant to include polypeptides, which comprise the amino acid sequence denoted by SEQ ID NO: 1, but differ in one or more amino acid residues in their overall sequence, namely, which have deletions, substitutions (e.g. replacement of at least one amino acid by another amino acid), inversions or additions within the overall sequence of SEQ ID NO: 1. This term also encompasses the replacement of at least one amino acid residue in the overall sequence by its respective D amino acid residue. Derivatives also encompass amino acid sequence denoted by SEQ ID NO: 1 in which at least one amino acid residue is replaced by a synthetic amino acid residues, an amino acid analog or an amino acid mimetic.

Amino acid "substitutions" are the result of replacing one amino acid with another amino acid, for example with another amino acid that has similar structural and/or chemical properties (conservative amino acid replacements). Amino acid substitutions may be made on the basis of similarity in polarity, charge, solubility, hydrophobicity, hydrophilicity, and/or the amphipathic nature of the residues involved. For example, each of the following eight groups contains amino acids that are conservative substitutions for one another:

1) Alanine (A), Glycine (G);
2) Aspartic acid (D). Glutamic acid (E);
3) Asparagine (N), Glutamine (Q);
4) Arginine (R), Lysine (K);
5) Isoleucine (1), Leucine (L), Methionine (M), Valine (V);
6) Phenylalanine (F), Tyrosine (Y). Tryptophan (W);
7) Serine (S), Threonine (T); and
8) Cysteine (C), Methionine (M).

Amino acid substitutions may also be made by replacing at least one amino acid residue of the sequence denoted by SEQ ID NO: 1 by at least one synthetic amino acid residue, as well as by at least one amino acid analog or amino acid mimetic, as defined above and as known in the art.

It is appreciated that these modified polypeptide fragments or derivatives must not alter the biological activity of the original peptide. By the term "functional" it is meant to encompass any fragment or derivative of the amino acid sequence denoted by SEQ ID NO: 1 which retains a biological activity qualitatively similar to that of the unmodified polypeptide (having the amino acid sequence denoted by SEQ ID NO: 1). The biological activity of the fragment or derivative as herein defined may be determined by any method known in the art, for example as described herein, namely by monitoring wherein said fragment or derivative increases expression of at least one cellular moiety as herein defined in cancer cells.

In particular embodiments the present disclosure relates to a functional fragment or derivative of the isolated polypeptide comprising amino acid sequence denoted by SEQ ID NO. 1, wherein said functional fragment or derivative has an amino acid sequence that is at least about 70%, 75%, 80%, 85%, 90%, more preferably 95%, in particular 99% identical to the amino acid sequence of the unmodified isolated polypeptide of the invention, namely to one of the amino acid sequences denoted by SEQ ID NO: 1, SEQ ID NO: 2 or SEQ ID NO: 3.

Therefore in various embodiments the present disclosure provides a method for treatment of cancer in a patient in need thereof, said method comprising administering to said patient an isolated polypeptide comprising the amino acid sequence denoted by SEQ ID NO: 1 or a functional fragment or derivative thereof and at least one anti-cancer agent, wherein the functional fragment or derivative is at least about 70%, 75%, 80%, 85%, 90% or 95% identical to the amino acid sequence denoted by SEQ ID NO: 1.

The isolated peptide and/or the anti-cancer agent of the present disclosure may be administered by any method known in the art per se or with a pharmaceutically acceptable carrier, diluent and/or excipient, as known in the art (for example phosphate buffered saline (PBS) or saline). In addition, any pharmaceutically acceptable salt or solvate of the isolated peptide as herein defined is encompassed by the present disclosure.

In other words, the isolated polypeptide and/or said at least one anti-cancer agent as herein defined are comprised in a pharmaceutical composition which optionally further comprises a pharmaceutically acceptable carrier, diluent and/or excipient. The isolated polypeptide and the anti-cancer agent may be comprised in separate pharmaceutical compositions or in the same pharmaceutical composition.

The pharmaceutical compositions of the present disclosure generally comprise a buffering agent, an agent which adjusts the osmolarity thereof, and optionally, one or more pharmaceutically acceptable carrier, diluent and/or excipient as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils.

In various embodiments the isolated polypeptide and/or said anti-cancer agent according to the present disclosure are administered at a therapeutically effective amount.

The term "therapeutically effective amount" as known in the art is intended to mean that amount of a drug or pharmaceutical agent (namely the isolated polypeptide and anti-cancer agent as herein defined) that will elicit the biological or medical response of a tissue, a system, animal or human that is being sought by a researcher, veterinarian, medical doctor or other clinician. Determination of a therapeutically effective amount is made by a skilled physician based on clinical parameters well known in the art.

Doses of APC1 that are therapeutically effective in humans may be assessed by a person of skill in the art by methods known in the art, for example by assays as exemplified herein below.

As shown in the Examples below, the peptide APC1 increased the responsiveness of cancer cells to various anti-cancer agents, including antibodies directed against the HER2/neu receptor, tamoxifen directed against the estrogen receptor and in addition doxorubicin and cis-platin, which act by other mechanisms of action. Therefore the present invention further provides a method for sensitizing cancer cells to at least one anti-cancer agent in a patient in need thereof, said method comprising administering to said patient an isolated polypeptide comprising the amino acid sequence denoted by SEQ ID NO: 1 or a functional fragment or derivative thereof, wherein said isolated polypeptide modulates expression of at least one cellular moiety in cancer cells in said patient, thereby sensitizing said cancer cells to said at least one anti-cancer agent.

By yet a further aspect the present invention provides an isolated polypeptide comprising the amino acid sequence denoted by SEQ ID NO: 1 or a functional fragment or derivative thereof for use in a method for sensitizing cancer cells to at least one anti-cancer agent in a patient in need thereof, wherein said isolated polypeptide modulates expression of at least one cellular moiety in cancer cells in said patient, thereby sensitizing said cancer cells to said at least one anti-cancer agent.

In specific embodiments the method for sensitizing cancer cells according to the invention is wherein said method further comprises administering said at least one anti-cancer agent to said patient.

In further specific embodiments the method for sensitizing cancer cells according to the invention is wherein said cancer is at least one of breast cancer, ovarian cancer, prostate cancer, lung cancer or colon cancer, B cell lymphoma, Acute Myeloid Leukemia (AML) or pancreatic cancer.

In still further specific embodiments of the method for sensitizing cancer cells to at least one anti-cancer agent in a patient in need thereof, said isolated polypeptide as herein defined is administered to colorectal cancer cells and lung cancer cells and transforms these cells to EGFR positive cells thereby rendering these cells sensitive to treatment with classical EGFR inhibitors, for example to monoclonal antibodies that bind EGFR and induce cell death.

In some embodiments the method of inducing differentiation of cancer cells as herein defined is performed in vivo and in other embodiments in vitro.

By the term "sensitizing" in the context of the present disclosure it is referred to a state in which cancer cells are made more prone, reactive, susceptible or responsive to a particular stimuli, in the present case to the effect of an anti-cancer agent targeting a cellular moiety as herein defend, by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%. 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 200%, 300%, 400%, 500%, 600%, 700%, 800%, 900% or about 1000% as compared to cells which were not treated with the isolated peptide as herein defined.

In particular it is referred to cancer cells that in the absence of administration of the isolated polypeptide of the present disclosure are naïve, insensitive or non-reactive to the effect of the an anti-cancer agent targeting a cellular moiety as herein defend. In various embodiments the isolated polypeptide as herein defined can transform prostate cancer cells that no longer respond to hormonal therapy and castrate to responding cells to hormonal therapy.

In further embodiments the isolated polypeptide according to the present disclosure transform lung cancer cells that do not respond to EGFR inhibitors to become responder cells (thereby sensitizing lung cancer cells that do not respond to EGFR inhibitors to EGFR inhibitors).

In still further embodiments the isolated polypeptide according to the present disclosure transform colorectal cancer (CRC) cells that do not respond to EGFR inhibitors to become responders (thereby sensitizing CRC cells that do not respond to EGFR inhibitors to EGFR inhibitors).

Particular but non-limiting examples for an anti-cancer agent that may be combined with the isolated peptide of the invention as herein defined include but are not limited to kadcyla. Herceptin, tamoxifen, cisplatin and doxorubicin.

By the term "Cancer cells" as used herein it is meant to encompass any type of cancer and any type of cancer cells derived therefrom.

Still further the present discourse provides a kit comprising:
 (i) an isolated polypeptide comprising the amino acid sequence denoted by SEQ ID NO: 1 or a functional fragment or derivative thereof and optionally a pharmaceutically acceptable carrier, diluent and/or excipient;
 (ii) an anti-cancer agent and optionally a pharmaceutically acceptable carrier, diluent and/or excipient.

In various specific embodiments the kit according to the invention relates to an anti-cancer agent that directly or indirectly interacts with said at least one cellular moiety. In further embodiments the kit according to the invention relates to an anti-cancer agent that is targeting a cellular moiety.

In some embodiments the kit according to the invention further comprises instructions for use.

In other embodiments the kit according to the invention relates to an anti-cancer agent that is an immunotherapy, a chemotherapeutic agent, a signal transduction inhibitor, a receptor inhibitor, a gene expression modulator, an apoptosis inducer, an angiogenesis inhibitor, a hormone therapy, a metabolic inhibitor, an anti-autophagy agent, endoplasmic stress inducer, reactive oxygen species (ROS) inducer or a combination thereof.

In further embodiments the kit according to the invention relates to an isolated polypeptide that consists of the amino acid sequence denoted by SEQ ID NO: 1.

The present disclosure further provides the kit as herein defined for use in a method of treating cancer in a patient in need thereof.

In various specific embodiments the isolated polypeptide as herein defined may be administered at a single dose. In further embodiments the isolated polypeptide as herein defined may be administered at multiple doses.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

The terms "comprises", "comprising", "includes", "including", "having" and their conjugates mean "including but not limited to". This term encompasses the terms "consisting of" and "consisting essentially of". The phrase "consisting essentially of" means that the composition or method may include additional ingredients and/or steps, but only if the additional ingredients and/or steps do not materially alter the basic and novel characteristics of the claimed composition or method. Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The present disclosure further provides a method of inducing differentiation of cancer cells comprising administering to said cells an isolated polypeptide comprising the amino acid sequence denoted by SEQ ID NO: 1 or a functional fragment or derivative thereof.

By the term "inducing differentiation" or "induction of differentiation" it is meant causing, generating, promoting or affecting changes in cell chemistry, inhibiting growth and promoting differentiation of cell type.

In some embodiments the isolated polypeptide as herein defined induces differentiation of cancer stem cells in the lung, colon, prostate or breast, such that these cells respond to classical targeted anti-cancer therapies of these diseases.

It should be noted that by the above embodiments reference is equally made to the various aspects of the invention, namely the method of treatment, method of sensitizing cancer cells, the isolated peptide and additional anti-cancer agent for use as well as to the kit of the invention.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures
Materials
Unless otherwise indicated herein below, the cell culture medium DMEM high glucose, L-Glutamine (Gibco 41965-039) or RPMI (Gibco cat #21875) comprised (per 500 ml) 50 ml FBS (Biological industries cat no. 04-121-1A), 5 ml Sodium Pyruvate 11 mg/ml (100 mM) (Biological industries cat no. 03-042-1B), 0.5 ml Amphotericin B 2500 µg/ml (Biological industries cat no. 03-029-1) and 5 ml Gentamycin sulfate 50 mg/ml (Biological industries cat no. 03-035-1).
Trypsin EDTA (Biological industries cat no. 03-052-1B).
Culture Flasks: 75 $cm^2$ (Nunc cat no. 178905), 25 $cm^2$ (Nunc cat no. 136196).
Chamber slide (8 wells, Nunc cat no. 154534).
APC1 (50 mg/ml in Phosphate Buffered Saline). The APC-1 peptide (Novetide, Israel) has the amino acid sequence of EKGAAFSPIYPRRK (denoted by SEQ ID NO: 1).
APC1 was solubilized by phosphate buffered saline (PBS).
Kadcyla, 100 mg (trastuzumab emtansine, Roche), 20 mg/ml solutions were prepared in 0.45% saline and used immediately.

Xylene (Sigma #534056).
Ethanol, anhydrous denatured, histological grade (100% Solufix #E003 and 95% Sigma #32294).
Deionized water (dH$_2$O).
Hematoxylin Gill2 (Sigma #GHS216).

Cells

The triple negative breast tumor cell lines MDA-MB-231 (grown with DMEM), MDA-MB-468 (grown with RPMI) and BTS-149 (grown with RPMI) were obtained from ATCC. The cells MDA-MB-231 and MDA-MB-468 are also refereed herein as "MDA231" and "MDA468", respectively.

Cell Culture Maintenance

Triple negative breast tumor cells (MDA-MB-231, MDA-MB-468 and BTS-149) were grown in an incubator at 37° C., 5% CO$_2$ until 70-80% density was reached (this density should not be exceeded). The growth medium was then discarded and the cell flask was washed with 5 ml Trypsin EDTA. Next, another amount of 5 ml Trypsin EDTA was added to the cell flask and the cell flask was placed in the incubator until most of the cells were no longer attached to the flask (the flask should not be tapped on to increase detaching of the cells; this procedure takes a few minutes). Then, medium (10 ml) was added to the Trypsin-treated cells. Finally, the cells suspended in medium and Trypsin were divided into 2 flasks and 15 ml fresh medium was added to each one of the flasks. The cells were placed in an incubator under the above conditions for 2-3 days until around 70-80% density was reached and the above procedure was repeated as necessary. The other cell lines used herein were grown as known in the art.

Cell Growth in the Presence of APC1

Cells (MDA-MB-231, MDA-MB-468 and BTS-149) were grown until 70-80% density was reached. Then the growth medium was discarded and the cells were treated with trypsin and medium as described above. After the cells were detached from the surface, the 20 ml cell suspension (namely cells in medium and Trypsin) were transferred into 50 ml conical tubes and centrifuged at 300 g for 10 min in 4° C. Next, the supernatant was discarded and 2 ml fresh medium were added to the cell pellet. Then the cells were fluidized and 13 ml medium was added to the tubes, thereby suspending the cells in a total of 15 ml medium. The cells were counted and seeded at 10.000-15,000 cells/well on chamber slide in 1 ml growing medium. The chamber slide seeded with cells was placed in the hood for 1 hour and then transferred to the incubator for an overnight incubation under the above conditions. The following day the medium was aspirated from the cell chamber slides and discarded and 1 ml cell treatment medium supplemented with APC1 (at a final concentration of 100 or 250 µg/ml) or control (medium only). Medium was added to each one of the wells (aliquots of APC1 were used in order to avoid repeated freeze-thaw cycle). The cells were then incubated for 24-144 hours. Optionally, additional dose(s) of APC1 were administered to the treated cells, and the cells were further incubated for up to 96 hours in the presence of the second dose and for up to 144 hours in the presence of the third dose. Cells were then collected and subjected to further analysis as detailed below.

Cell Growth in the Presence of APC1 and Kadcyla

Cells were grown until 70-80% density was reached. Then the growth medium was discarded and the cells were treated with trypsin and medium as described above. The cells that were suspended in medium and Trypsin were then transferred into 50 ml conical tubes and centrifuged at 300 g for 10 min in 4° C. Next, the supernatant was discarded and 2 ml fresh medium was added to the cell pellet. The cells were fluidized and additional 13 ml medium was added to the cells such that the cells are suspended in a total of 15 ml medium. The cells were counted and around 40,000 cells were placed in each one of nine 25 cm$^2$ flasks in 10 ml medium (in each flask). Cells were placed in the incubator overnight. The next day, the supernatant was discarded and replaced by 10 ml DMEM or RPMI containing 2.5% FBS (instead of 10% FBS). The cell flasks were further treated for example as follows:

Flasks 1+9: no treatment
Flask 2: 250 µg/ml APC1
Flask 3: no treatment
Flask 4: no treatment
Flask 5: no treatment
Flask 6: 250 µg/ml APC1
Flask 7: 250 µg/ml APC1
Flask 8: 250 µg/ml APC1

Cells treated as indicated above were incubated in an incubator for 48 hours. Then, a second dose of APC1 (at the same final concentration) was added to cell flasks 2, 6, 7 and 8 and the cells were further incubated for 24 hours. If the cells reached over 85% confluence, 50% of the cells were scraped from the flask. The media was discarded, and 10 ml DMEM or RPMI containing 10% FBS were added to each flask. The cell flasks were further treated for example as follows (with a third dose of APC and/or Kadcyla):

Flasks 1+9: no treatment
Flask 2: 250 µg/ml APC1
Flask 3: 5 µg/ml Kadcyla
Flask 4: 10 µg/ml Kadcyla
Flask 5: 25 µg/ml Kadcyla
Flask 6: 250 µg/ml APC+5 µg/ml Kadcyla
Flask 7: 250 µg/ml APC1+10 µg/ml Kadcyla
Flask 8: 250 µg/ml APC1+25 µg/ml Kadcyla (optionally)

Cells were incubated for further 72-96 hours. Finally the cells were collected and subjected to analysis (FACS analysis of apoptosis markers, or assessment of HER2 expression) as described below. Kadcyla (trastuzumab emtansine, Roche) was weighted and diluted in 0.45% saline to a concentration of 20 mg/ml and used immediately (remaining solution was discarded).

In other words, the cells were incubated with a first dose of APC1 for 48 hours, then incubation with a second dose of APC1 for 24 hours, next the medium was removed, fresh FBS medium was added along with a third dose of APC1 at the same original dose with or without Kadcyla where indicated. After 72 hours the cells were sent to FACS analysis.

Resazurin Cell Viability Assay of MDA-MB-231 Cells Treated with APC1 and Tamoxifen Materials Clear bottom 96 well cell culture plates;
Cell Culture Media, 10% FBS in DMEM comprising Sodium Pyruvate, Penicillin/Streptomycin and Amphotericin B;
Cell Cytotoxicity Assay Kit (Colorimetric) ab112118;
Tamoxifen (Sigma T5648) diluted to 2.5 mg/ml (6.65 mM);
50 mg/ml Stock APC1 solution: Diluted in PBS;
Cell Lines: MDA-MB-231 cells and MDA-MB-231 cells treated with APC1 at 250 µg/ml 2 times a week for 1 week unless otherwise indicated.

Procedure

MDA-MB-231 or MDA-MB-231 treated with APC1 were seeded at 10$^3$ cells per well in 96 well plate in cell culture media (100 µl). Cells treated with APC1 were seeded with 250 µg/ml APC1 and incubated overnight. Then, the following treatments solutions were prepared in culture media with or without 250 µg/ml APC1: Control, 10 nM Tamoxifen, 50 nM Tamoxifen and 100 nM Tamoxifen. Next the media was aspirated from the plates, and treatment solutions (100 µl) was added to the appropriate wells.—Each treatment was performed in triplicates and the cells were incubated for 48 hours. Then 20 µl of Cell Cytotoxicity Assay Kit (Colorimetric, ab112118) was added to each well, and the cells were incubated for 1 hour The plates were read at 570 and 6050D in a spectrophotometer.

Next, the percentage of cell viability was calculated for samples and controls based on the following formula: % Cell viability=100×(Rsample−Ro)/(Rctrl−Ro). "Rsample" is the absorbance ratio of OD570/OD605 in the presence of the test compound (APC1). "Rctrl" is the absorbance ratio of OD570/OD605 in the absence of the test compound (Control) and "Ro" is the averaged background (non-cell control) absorbance ratio of OD570/OD605.

Cell Viability Assay (Resazurin) of MDA-MB231 Cells Treated with APC1 and Cisplatin, or Doxorubicin
Materials
Clear bottom 96 well cell culture plates;
Cell culture media was 10% FBS in DMEM comprising sodium pyruvate, penicillin/streptomycin and amphotericin B;
Cell Cytotoxicity Assay Kit (Colorimetric) ab112118;
Cisplatin (Sigma EPCC221000), freshly diluted to 40 mg/ml (133.3 mM) in DMSO.
Doxorubicin (D1515 Sigma), diluted to 50 mg/ml (86.6 mM) in DW (kept at 4° C. for up to 3 weeks).
APC1, 50 mg/ml diluted in PBS;
Cell Lines were MDA-MB-231 cells, MDA-MB-231 cells treated with APC (250 µg/ml, 2 times a week for 1 week), MDA-MB-468 cells and MDA-MB-468 cells treated with APC1 (250 µg/ml 2 times a week for 1 week).
Procedure Cells ($10^3$) were seeded in 96 well plate in cell culture media (100 µl). Cells treated with APC1 were seeded with APC1 at 250 µg/ml. The cells were incubated overnight. Then the following treatments solutions were prepared in culture media with or without 250 µg/ml APC1: Control, 500 µM Cisplatin, 750 µM Cisplatin, 1000 µM Cisplatin, 0.3 µM Doxorubicin, 0.5 µM Doxorubicin and 1 µM Doxorubicin.

Then the media was aspirated from the plates, and 100 µl of the treatment solutions were added to the appropriate wells, each treatment in triplicates. The cells were incubated for 48 hours. Next, 20 µl of Cell Cytotoxicity Assay Kit (Colorimetric, ab112118) were added to each well, and the cells were incubated for 1 hour and read at 570 and 6050D in a spectrophotometer. The percentage of cell viability for samples and controls was calculated as detailed above, based on the following formula: % Cell viability=100× (Rsample-Ro)/(Rctrl-Ro).

Fluorescence-Activated Cell Sorting (FACS) Analysis

Cells were examined for apoptosis or HER2 expression using FACS analysis. The HER2 antibody used was abcam ab16901. The marker Annexin (Enco) was used for assessment of apoptosis.

Immunofluorescence of Human Tumor Cells Treated with APC1

Materials used for Immunofluorescence of human tumor cells treated with APC were as follows. Slides: Nunc™ Lab-Tek™ II CC2™ Chamber Slide System (154917 Nunc), Washing Buffer: PBS (02-023-5A Biological Industries), Fixing Solution: 3% Formaldehyde (252549 Sigma) in PBS, Permeabilization Solution: 0.25% Triton X-100 (0694 Amresco) in PBS, Blocking/Antibody buffer: 1% BSA (A7906 Sigma) in PBS with 0.1% Tween-20 (0777 Amresco), First Antibody: Anti-ErbB 2 antibody (3B5) (ab16901) abeam, Secondary Antibody: Donkey Anti-Mouse IgG H&L (Alexa Fluor® 488) preadsorbed (ab150109), Mounting media with DAPI (4',6-diamidino-2-phenylindole): Fluoroshield Mounting Medium With DAPI (abcam ab104139).

After incubating cells with APC1 as detailed above, the medium was aspirated and the cells were washed by filling each well with washing buffer. The buffer was discarded and 300 µl fixing solution was added to each well and the cells were incubated at room temperature (RT) for 15 minutes. The fixing solution was then discarded, the well was briefly rinsed twice with washing buffer and 300 µl Permeabilization solution were added to each well. The cells were then incubated at RT for 10 minutes. Next, the solution was discarded, and the wells were treated by adding washing buffer to each one of the wells and by waiting five minutes before discarding the washing buffer from the wells. After the washing was completed, Blocking buffer (1 ml) was added to each well, and the cells were incubated at RT for 1 hr. Before the end of the incubation time, the first (primary) antibody was diluted, namely the Anti-ErbB 2 antibody (3B5) (ab16901) abeam was diluted 1:400 in antibody dilution buffer. Then the blocking buffer was discarded from the wells and 120 µl primary antibody was added to each well. The cells were covered (by Parafilm or duct tape) and incubated overnight at 4° C. The next day, the primary antibody was discarded and the cells were washed three times with washing buffer (five minutes for each wash, as described above). Then the secondary antibody was diluted, namely the Donkey Anti-Mouse IgG H&L (Alexa Fluor® 488) preadsorbed (ab150109) was diluted 1:1000 in antibody dilution buffer and 150 µl secondary antibody was added to each well. The cells were incubated at RT for 1 hour, in the dark. The cells were then washed three times with washing buffer (five minutes for each wash in the dark, as described above). The wells were then removed from the slide, and the slide was air dried in the dark. Mounting media with DAPI was added, the chambers were removed from the slide, then mounting media was added onto slide, covered with coverslip, sealed with nail polish and stored in the dark at 4° C. Cells were visualized in a fluorescent microscope with filters for Alexa fluor 488 (green emission) and DAPI (blue emission).

Preparation of Cancer Cells Culture for Injection into Balb/C Nude Mice

MDA-MB-231 cells were grown in DMEM medium with Hepes (Gibco 41965-039) containing 10% heat inactivated Fetal Bovine Serum (Biological industries, #04-121-1A) and 1% Pen-Strep antibiotic (Biological industries, 03-031-1B) inside a 175 cm² flask (Nunc 178883). The cells were incubated at 37° C. in the presence of 5% $CO_2$ and 95% humidity. The other cancer cells injected into mice (namely OV90 and Panc1) were prepared in a similar manner.

When a sufficient number of cells were present, the cells were centrifuged at 300 g for 5 minutes. The supernatant was discarded and 5-10 ml PBS (Biological Industries, #02-023-5A) was added to the cell pellet in order to wash the remaining medium. The cells were centrifuged again (same speed and time), the supernatant was discarded and 5-10 ml Saline was added to the cells. At this stage the cells were counted under a light microscope using a Hemocytometer, and saline was accordingly added to reach a concentration of $8\times10^6$ cells/200 µl.

Experimental Animals

Female Balb/C Nude mice (BALB/cOlaHsd-Foxn1nu, 5-6 weeks old) were purchased from Harlan laboratories.

Prior to purchase, mice were maintained in a pathogen free environment. Cages (425×266×185 mm–floor area 800 cm$^2$ (1291H Eurostandard Type III H. Tecniplast, 6-9 mice in each cage) were cleaned and sawdust (Harlan Telkad Sani-Chips, 2.2 Cu. Ft. Laboratory grade) and water (Tap water in IL bottles) were replaced once a week. Mice were identified using a sterilized ear punch.

Cancer Cell Injection of Balb/C Nude Mice

Female Balb/C Nude mice (as detailed above) were retained in the Inventor's animal facility for at least 24 hours. Next all mice were intraperitoneally injected with 8×10$^6$ cells (in 200 μl saline) using a 27 G needle.

APC1 Treatment of Mice

APC1 peptide was diluted in saline to the appropriate concentration in order to inject a dose of 350 μg/mouse. After the tumors reached the size of 0.5 cm×0.5 cm (usually 5 days) treatment of mice began. The control group was injected with aaline. The treated group was injected with APC1 (at 350 μg per mouse). The mice were injected on Sunday, Tuesday and Thursday for 2 weeks (6 injections total).

Monitoring of Tumor Size and Mice Weight

During the treatment period, each mouse was weighted, and the tumor size was measured by Digital caliper.

HER2 Immunohistochemistry of Tumor Sections

Solutions and Reagents

The following solution and reagents were used: Wash Buffer: 1×TBS/0.1% Tween-20 (1× TBST), for preparing 1 L 50 ml 20×TBS (Amresco #J640) were added to 950 ml distilled H$_2$O (dH$_2$O). Then 1 ml Tween-20 (Amresco #J640) was added to the solution and the solution was mixed. Antibody Diluent: SignalStain® Antibody Diluent #8112. Antigen Unmasking: Citrate: 10 mM Sodium Citrate Buffer, for preparing 1 L 2.94 g sodium citrate trisodium salt dihydrate (C$_6$H$_5$Na$_3$O$_7$·2H$_2$O) was added to 1 L dH$_2$O and the pH was adjusted to 6.0. Hydrogen Peroxide (3%): 10 ml 30% H$_2$O$_2$(Sigma #216763) were added to 90 ml dH$_2$O. Blocking Solution: Background Buster (Innovex #NB306). Primary (1$^{st}$) antibody: Anti-ErbB 2 antibody [3B5] (ab16901) (abcam). Fluorescent Secondary antibody: Donkey Anti-Mouse IgG H&L (Alexa Fluor® 488) preadsorbed (ab150109). Mounting media with DAPI: Fluoroshield Mounting Medium With DAPI (abcam ab104139).

Deparaffinization and Rehydration

Slides were not allowed to dry at any time during this procedure. Sections were prepared by Harlan laboratories—Fixed section were parafised, cut to 4 micron sections, and attached to glass slides. In order to deparaffinize/hydrate the sections, sections were incubated in three washes of xylene for 5 minutes each, two washes of 100% ethanol for 10 minutes each, two washes of 95% ethanol for 10 minutes each and finally washed twice in dH$_2$O for 5 minutes each.

Antigen Unmasking

Slides were boiled in 10 mM sodium citrate buffer at pH 6.0 and then maintain at a sub-boiling temperature for 10 minutes. Slides were allowed to cool on the bench top for 30 minutes.

Staining

Sections were washed in dH$_2$O three times for 5 minutes each. Sections were incubated in 3% hydrogen peroxide for 10 minutes and then washed in dH$_2$O twice for 5 minutes each and in wash buffer for 5 minutes. Each one of the sections was blocked with 100-400 μl blocking solution for 30 minutes at room temperature. Next, the blocking solution was removed and 100-400 μl primary antibody diluted 1:400 in antibody diluent was added to each section and the section were incubated overnight at 4° C. Then the antibody solution was removed and the sections were washed in wash buffer three times for 5 minutes each. The secondary antibody was diluted 1:1,000 in antibody diluent, and 100-400 μl secondary antibody was added to each one of the sections. The sections were then incubated 1 hour at room temperature in the dark. Finally, the secondary antibody solution was removed and the sections were washed three times with wash buffer for 5 minutes each, in the dark and in dH$_2$O for 5 minutes in the dark.

Dehydrate Sections

The slide mounted with the sections was air dried in the dark. Coverslips were mounted using mounting media.

Western Blot Analysis of Notch Protein Receptor

MDA-MB-231 cells (0.8×10$^6$) were seeded on five 75 cm$^2$ flasks in 25 ml DMEM (41965039 Gibco) medium comprising 10% fetal bovine serum (FBS), Gentamycin Sulfate (03-035-1C Biological industries) and Amphotericin B (03-029-1C Biological industries). Cells were incubated overnight in an incubator. Then the peptide APC1 at 50 mg/ml in PBS stock solution was thawed at room temperature (R.T.) and added to the flasks to a final concentration of 250 μg/ml and the cells were incubated for 0, 1, 3, 5 or 21 hours.

Media was then removed and the cells were scrapped off the flask by a cell scraper into 1.8 ml fresh DMEM media. Cells were collected into 2 ml Eppendorf tubes in two fractions: cytosolic proteins and membrane proteins that were extracted by Membrane Protein Extraction Kit (Thermo scientific #89842). Protease inhibitors (Sigma p2714) and phosphatase inhibitors (Sigma P5726) were added to the Permeabilization and Solubilization Buffers, as recommended by the manufacturer.

Samples were prepared for western blotting as follows: sample buffer (invitrogen cat #NP0007, 4-fold concentrated) and sample reducing agent (Invitrogen cat #NP0009, 10-fold concentrated) were added to each sample and the samples were boiled for 5 minutes.

Samples were then loaded onto a 4-20% Tris-Glycin gel (NuSep cat #NG21-420), 50 μl was loaded into each well. The gel was ran for 1 hour at 150V (first 10 min at 80V), then was transferred onto a PVDF membrane (Immobilon-P Transfer Membrane Cat #:IPV00010-PORE SIZE:0.45) for 1 hour. The membrane was blocked for 1 hour using 5% milk in TBST at R.T with agitation. Notch3 antibody (abcam ab23426) was added at 1:1000 dilution in 5% milk in TBST, and incubated overnight at 4° C., with agitation.

The membrane was washed 3 times using TBST, and the secondary antibody αRabbit-HRP was then added (dilution 1:5000 in 5% milk in TBST) for an incubation of 1 hour at room temperature, with agitation. Finally, the membrane was washed 3 times using TBST (4-5 minutes were allowed between each wash) and ECL substrate was added (Clarity Western 1705061 BIO-RAD). The membrane was scanned using a Li-COR C-Digit device. Notch 3 antibody was applied to the membrane and the quantitation of the protein was preformed and calibrated with beta-actin protein.

Gluthation Reductase Determination in Cells Treated with APC1

Materials 75 cm$^2$ cell culture flasks:

Cell culture media was 10% FBS in DMEM comprising sodium pyruvate, penicillin/streptomycin and amphotericin B:

Gluthatione Assay Kit (Sigma CS0260);

APC1 solution, 50 mg/ml in PBS:

Cell lines (MDA-MB-231, MDA-MB-468) were grown in 75 cm$^2$ cell culture flask, reached 80-90% confluence. The cells were treated with APC1 (250 μg/ml, 2 times per week for 1 week).

Procedure

Cells were washed twice with 10 ml PBS, PBS (5 ml) was added and the cells were collected by scrapping, centrifuged at 300G, 4° C. for 5 minutes, the supernatant was then discarded and the cells were treated with APC1 as indicated above. The values of the Glutathione Standard Solutions were used to determine the standard curve and the delta A412/min equivalent to 1 nmole of reduced glutathione per well was calculated according to manufacturer's instructions.

Example 1

Treatment of Triple Negative Breast Cancer Cells with APC1 Increases Expression of HER2 Receptor on the Cell Surface As indicated above, triple negative breast cancer (TNBC) is defined inter alia by the lack of expression of estrogen receptor (ER) and progesterone receptor (PR) and the lack of expression or amplification of human epidermal growth factor receptor 2 (HER2).

The peptide termed herein "APC1", having the amino acid sequence EKGAAFSPIYPRRK (denoted by SEQ ID NO: 1), consists of the 14 C-terminal amino acid residues of the peptide KTPAF50 that was previously found to affect viability and proliferation of cancer cells in vitro and in mice (3, 4). The effect of administration of APC1 to MDA-MB-231 cells that are known to be triple negative breast cancer cells (and do not express HER2) was first examined by FACS analysis, as described above, and is demonstrated in FIG. 1.

Briefly, APC1 was administered to MDA-MB-231 cells as detailed above, in multiple doses. A first dose of APC1 (at a final concentration of 100 or 250 μg/ml) was added to the cells and the cells were incubated for 48 hours. Then an additional dose of APC1 was administered to the treated cells and the cells were further incubated for 24 hours.

Figure 1A:
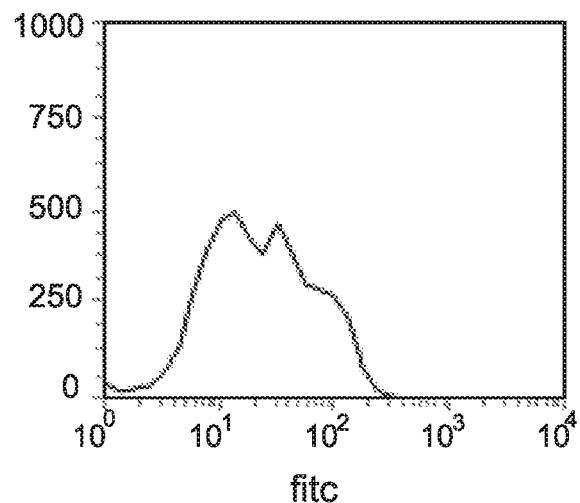
FIG. 1A-FIG. 1D: FACS analysis of HER2 in MDA-MB-231 cells
Figure 1B:
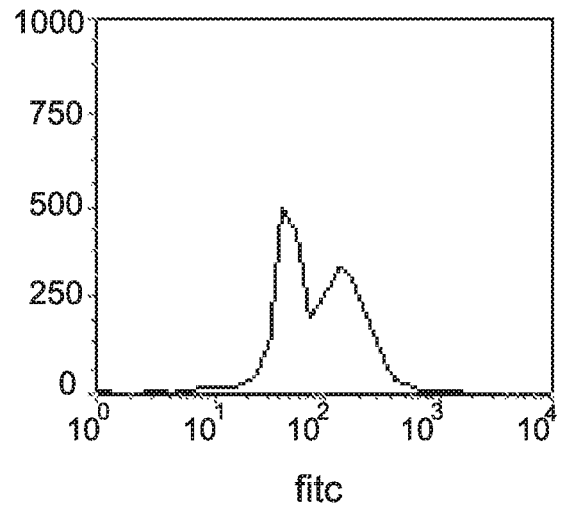
Figure 1C:
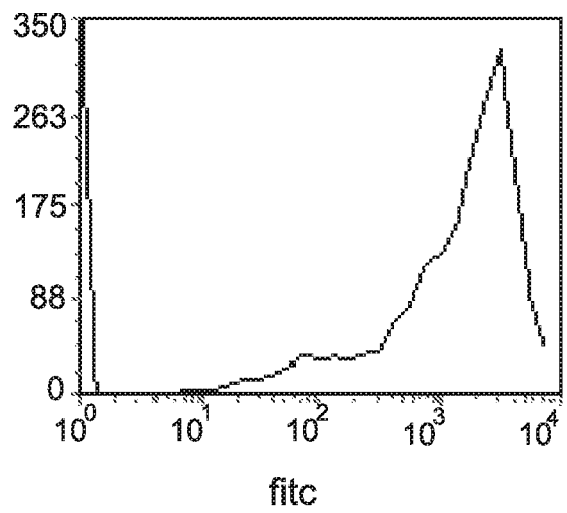
Figure 1D:
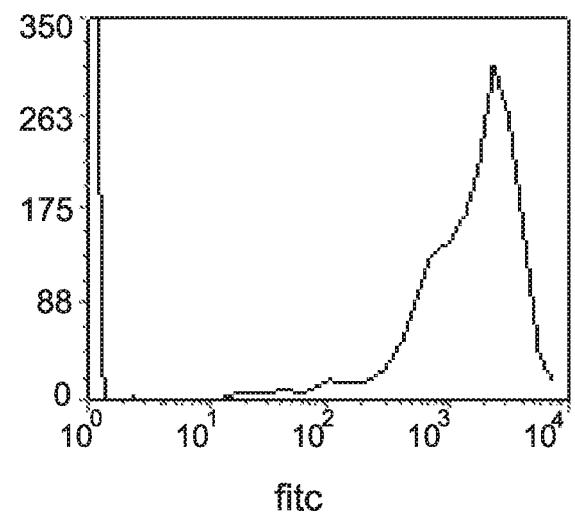

As shown in FIG. 1A, there is almost no expression of HER2 on cell membranes of MDA-MB-231 cells in the absence of APC1 treatment (control cells). Surprisingly, in MDA-MB-231 cells treated with APC1 there is a rise in HER2 expression, as demonstrated in FIG. 1B and FIG. 1C. This effect is concentration dependent as deduced from a shift in HER2 expression when comparing FIG. 1B (at 100 μg/ml APC1) to FIG. 1C (at 250 μg/ml APC1). Apparently, at 250 μg/ml APC1, HER2 expression on the cell surface of MDA-MB-231 cells is similar to its expression on N87 cells, which are known to be positive for HER2 (FIG. 1D).

The effect of APC1 administration on HER2 expression on TNBC cells was further examined by immunofluorescence of HER2 expression of MDA-MB-231 and MDA-MB-468 cells treated with APC at various concentrations and for various incubation periods, as detailed above.

First, as demonstrated in FIG. 2B, MDA-MB-231 cells incubated in the presence of 250 μg/ml APC for 48 hours showed clear HER2 expression when analyzed by immunofluorescence of HER2 expression and when compared to the control cells (FIG. 2A).

In addition, as shown in FIG. 3B, the above effect was enhanced when MDA-MB-231 cells were incubated in the presence of three doses of 250 μg/ml APC1 and prolonged incubation periods, namely 144 hours of incubation after the initial dose and additional 96 and 72 hours of incubation after the second and the third doses, respectively. The above indicated conditions with a dose of 250 μg/ml APC1 was found to be optimal for increasing HER2 expression for the present cell type.

Similar results were obtained for other known TNBC cells, namely MDA-MB-468, as demonstrated in FIG. 4B. In this case the cells were administered with two doses of APC1 (100 μg/ml each) and were subjected to incubation periods of 24 and 72 hours after the first and the second dose, respectively.

Notably, in all of the control cells that were not administered with APC1, no HER2 expression was observed by immunofluorescence (as demonstrated in FIG. 2A, FIG. 3A and FIG. 4A).

The above results indicate that administration of APC1 increases HER2 expression on the cell surface, and therefore without wishing to be bound by theory, renders the treated cells more sensitive (or vulnerable) to treatment targeting HER2.

Example 2

The Effect of Kadcyla on MDA-MB-231 Cells Treated with APC1

The above results demonstrate that administration of APC1 to TNBC cells enhances or increases HER2 expression at least on the cell surface and that APC1 may thus be used as an agent that increases the susceptibility of these cells to any treatment targeting HER2, for example antibodies directed to HER2.

In order to examine whether APC1 indeed increases the susceptibility of TNBC cells to treatment targeting HER2, MDA-MB-231 cells were first administered with APC1 and then with Kadcyla, as described above. Kadcyla is an antibody-drug conjugate (ADC) that combines the mechanisms of action of trastuzumab (an antibody directed to HER2, also known as Herceptin) and the chemotherapeutic molecule emtansine (DM1), in one medicine.

Briefly, cells were first administered with two doses of APC1 (250 μg/ml each, with incubation periods of 48 and 24 hours after the first and second administration, respectively) and were further administered with Kadcyla at 5 or 10 μg/ml (and incubated for further 72 hours). The treated cells were then subjected to FACS analysis of the apoptosis marker Annexin.

MDA-MB-231 cells are known to be triple negative cells as detailed above and therefore not sensitive to Kadcyla treatment. Indeed, as demonstrated in FIG. 5A, the level of apoptosis as a result of administering Kadcyla alone to MDA-MB-231 cells that were not pre-treated with APC1 was relatively low (practically none when administered with 5 μg/ml Kadcyla and 10% when administered with 10 μg/ml Kadcyla).

Surprisingly, in cells treated with both APC1 and Kadcyla, the level of apoptosis was at least 2.5 times greater than in cells treated with Kadcyla alone for each one of the Kadcyla doses used. Without wishing to be bound by theory, APC1 allowed Kadcyla to enter the cells and release the drug moiety that acts as a cell death factor.

Similar results were obtained for MDA-MB-231 cells that were first administered with APC1 and then with Kadcyla as described above, when Kadcyla was administered at 5, 10 or 25 μg/ml, as demonstrated in FIG. 5B. In this case however, the level of apoptosis in cells treated with both APC1 and Kadcyla was 3-10 times greater than in the respective cells that were only treated with APC1.

In order to further substantiate the effect of administering APC1 to TNBC cells for their sensitization to further treatment with anti-HER2 agents, additional experiments were performed in MDA-MB-231 cells as well as in other TNBC cells, namely MDA-MB-468 and BTS49.

In these experiments APC1 was administered twice (at 250 µg/ml each) with incubation periods as detailed above. Then Kadcyla was administered at 5, 10 or 25 µg/ml and the cells were further incubated as detailed above.

FIG. 6 demonstrates 2-6 fold higher apoptosis level in MDA-MB-231 cells pretreated with APC1 prior to treatment with Kadcyla. In the control and APC1/Kadcyla only treated cells there was a low level of apoptosis, while in cells treated with both APC and Kadcyla there was a significant increase in the level of cellular apoptosis.

In addition FIG. 7 shows 2.5-5 fold higher apoptosis level in BTS49 cells pretreated with APC1 prior to treatment with Kadcyla, similar to the results shown for MDA-MB-231 cells. However, in the case of MDA-MB-468 cells, the basal level of apoptosis obtained in cells that were not pre-treated with APC1 was rather high.

Example 3

Expression of HER2 Receptor on MDA-MB-231 Tumor Cells in Mice Treated with APC1

APC1 was also shown to increase the expression of HER2 on TNBC cells (MDA-MB-231) in mice injected with the tumor cells, as detailed below.

Female Balb/C Nude mice (5-6 weeks old) were intraperitoneally injected with $8\times10^6$ MDA-MB-231 cells. After the tumors reached the size of 0.5 cm×0.5 cm (usually after five days) mice were injected with APC1 (350 µg per mouse) three times per week, for two weeks (namely on Sunday, Tuesday and Thursday for 2 weeks, 6 injections total).

In order to monitor the effect of APC1 on MDA-MB-231 tumor cells grown in mice, HER2 Immunohistochemistry of tumor sections was performed. As demonstrated in FIG. 8, while in control cells (FIG. 8A, obtained from mice treated with saline) there was no observed expression of HER2 on the cell surface, in cells obtained from mice treated with APC1 (FIG. 8B) there was a clear HER2 expression.

In view of the above and without wishing to be bound be theory, APC1 caused HER2 to be expressed on the cell surface, rendering these cells vulnerable or sensitive to HER2-based anti-cancer therapy directed to HER2.

Example 4

The Effect of Herceptin on MDA-MB-468 Cells Treated with APC1

As demonstrated above, APC1 increased expression of HER2 on cells and thereby allowed specific targeting of cells by HER2-based antibody treatment of cancer. In order to demonstrate the ability of a further HER2 based anti-cancer agent to target TNBC cells that were pre-treated with APC1, Herceptin, a monoclonal antibody that interferes with the HER2/neu receptor, was used.

FIG. 9 shows that in the TNBC cells MDA-MB-468 treated with both APC1 and Herceptin the level of apoptosis was higher (25%) as compared to the apoptosis level in cells treated with Herceptin only (10%) or with APC1 only (15%). Moreover, the level of apoptosis in MDA-MB-468 cells treated with a combination of both APC1 and Herceptin was comparable to the level of apoptosis in N87 cells treated with Herceptin alone.

Example 5

Treatment of TNBC Cells with APC1 Increased Expression of the Notch3 Protein

As known in the art, Neurogenic locus notch homolog protein 3 (Notch3) is overexpressed in several types of cancers and is currently being investigated as a target for anti-cancer drugs. The effect of administering APC1 on the level of Notch3 was assayed in the TNBC cells MDA-MB-231, as detailed above.

As demonstrated in FIG. 10, upon administration of APC1 to MDA-MB-231 cells there was an increase in expression of active Notch3 receptor on the cell membrane, as shown by the western blot analysis of the membrane protein fraction that was highest for incubations periods of 3 and 5 hours.

This result further demonstrates the ability of the peptide APC1 to induce expression of a cellular protein a membrane protein in the above case.

Example 6

Treatment of TNBC Cells with APC1 Rendered the Cells Sensitive to Tamoxifen

TNBC cells were incubated in the presence of APC in order to examine whether APC1 also modulates expression of estrogen receptors. To this end MDA-MB-231 cells were pre-treated with APC1 and then incubated in the presence of tamoxifen for 24-48 hours. Viability of these cells was then examined by a resazurin cell viability assay, as detailed above.

As demonstrated in FIG. 11B, MDA-MB-231 cells treated with APC1 (at three doses of 250 µg/ml) and tamoxifen (for 24 hours) showed reduced viability when compared to the control cells shown in FIG. 11A that were not pre-treated with APC1 and were grown in the presence of tamoxifen alone.

Reduction in viability was more pronounced when the MDA-MB-231 cells were treated with APC1 (at three doses of 250 µg/m) and tamoxifen for 48 hours, as evident from comparing FIG. 12B to FIG. 12A.

The reduction in viability observed in MDA-MB-231 cells treated with a combination of APC1 and tamoxifen as compared to MDA-MB-231 cells that were not treated with APC1 illustrates, without being bound by theory, a clear effect of APC1 on the target of tamoxifen, namely estrogen receptors. In other words, these results show that APC1 increases expression of estrogen receptors in cancer cells, rendering these cells more sensitive to tamoxifen.

Example 7

Treatment of MDA-MB-231 Cells with APC1 Increased Expression of Estrogen Alpha Receptor In view of the results shown above, the expression level of estrogen receptor alpha was directly assayed. As demonstrated in FIG. 13, a western blot analysis performed with an anti-estrogen receptor alpha (ER alpha) antibody showed a clear increase in the expression level of estrogen receptor alpha in MDA-MB-231 cells treated with APC1 (250 µg/ml) once a week for one week (lanes 3 to 7 from the left in FIG. 13) or twice a week for 3 or 4 weeks (lanes 9, 10 from the left in FIG. 13).

These results further illustrate that APC increases expression of a cellular moiety in cancer cells, this time the estrogen receptor.

Example 8

APC1 Increased the Sensitivity of TNBC Cells to Chemotherapy

Further to the above results showing that APC increases the sensitivity of TNBC cells to treatment with agents directed to specific cellular targets, the following results show that APC1 also increased the sensitivity of TNBC cells to other anti-cancer agents which act by different mechanisms of action.

To that end, the TNBC cells MDA-MB-231 and MDA-MB-468 were pre-incubated with APC1 and then incubated in the presence of doxorubicin or cisplatin, as detailed above. As shown in FIG. 14A. APC1 increased the sensitivity of the above TNBC cells to doxorubicin, in a concentration dependent manner.

A similar effect was shown for a combination of APC1 and cisplatin, as shown in FIG. 14B.

Example 9

APC1 Increased the Sensitivity of TNBC Tumors to Doxorubicin

Further to the above results showing that the administration of APC1 increases sensitivity of TNBC cells to doxorubicin or cisplatin, the effect of a combination of APC and doxorubicin was also assayed in mice inoculated with human TNBC cells (tumor).

To this end, mice were inoculated with TNBC cells as detailed above, briefly 32 nude mice were inoculated subcutaneously with TNBC cells (MDA-MB-231, $8 \times 10^6$ cells per mouse). When the tumors exceeded a volume of 50 $mm^3$, the mice were randomly divided into four groups of 8 mice each, as follows. A control group was treated with saline only, the APC1-treated group was treated three times a week with APC1 at doses of 15 mg/kg, the doxorubicin and APC1 treated group was treated twice a week with doses of APC (at 15 mg/kg) and once a week with doxorubicin (at 3 mg/kg) and the doxorubicin-treated group was treated with doxorubicin only, once a week at a dose of 3 mg/kg. These dosing protocols were repeated throughout the experiment, namely for 5 weeks.

As clearly shown in FIG. 15, while in the control group the relative tumor volume increased linearly, in the doxorubicin-treated and in the APC1-treated groups there was a moderate increase in tumor volume (the effect was more pronounced for the APC1-treated group).

Remarkably, in mice treated with both APC1 and doxorubicin there was a clear synergistic effect on tumor volume, resulting in inhibition of tumor growth and even a reduction in the size of the tumor (relative to its original size).

These examples clearly show that APC1 increases the sensitivity of TNBC cells to chemotherapy per se or when present as a tumor in an animal.

Example 10

Combination of APC1 and Doxorubicin for Treatment of Ovarian and Pancreatic Tumors In view of the effect of the combination of APC1 and doxorubicin on TNBC tumors, the inventors have also investigated the effect of the above combination on tumors derived from other cancers, namely human ovarian cancer and human pancreatic cancer.

To this end, nude mice were inoculated subcutaneously with human ovarian cells (OV90, $9 \times 10^6$ cells per mouse) or human pancreatic cancer cells (Panc1, $7 \times 10^6$ cells per mouse). When the tumors exceeded a volume of 40 $mm^3$ or 50 $mm^3$ (for OV90 and Panc1, respectively), the mice were randomly divided into four groups of 8 mice each, as follows. A control group was treated with saline only, the APC1-treated group was treated three times a week with doses of APC1 at 15 mg/kg each, the doxorubicin and APC treated group was treated twice a week with doses of APC1 (at 15 mg/kg each) and once a week with doxorubicin (at 3 mg/kg) and the doxorubicin-treated group was treated with doxorubicin only, once a week at a dose of 3 mg/kg. These dosing protocols were repeated throughout the experiment, namely for 5 weeks.

As shown in FIG. 16, while in the control group the relative tumor volume increased linearly, in the doxorubicin-treated and in the APC1-treated groups there were modest increases in tumor volume and the effect was more pronounced for the APC1-treated group.

Surprisingly, in mice treated with both APC1 and doxorubicin there was a clear synergistic effect on tumor volume, resulting in inhibition of tumor growth (by day 20) and a reduction in tumor size relative to the original tumor size from day 20 to the end of the experiment.

A similar synergistic effect was shown for human pancreatic cancer tumor cells inoculated into mice, as shown in FIG. 17.

Example 11

APC1 Decreased Glutathione Level in Human Cancer Cells

As well known in the art, glutathione conjugation and transport of glutathione conjugates of anticancer drugs out of cells was suggested as one of the mechanisms for detoxification of anticancer drugs.

Generally, glutathione may combine with anticancer drugs to form less toxic and more water soluble conjugates. Indeed, glutathione-related enzymes have been found to be increased or overexpressed in many drug resistant cells, resulting in drug resistance.

In the present example the inventors have investigated the effect of APC1 on the level of glutathione in ovarian, pancreatic and TNBC cancer cells.

As detailed above, the ovarian cancer cells OV90 and OV3, the pancreatic cancer cells BxPC3 and Panel and the TNBC cancer cells MDA-MB-231 and MDA-MB-468 were treated with APC1 and then the relative glutathione levels in these cells was measured as detailed above.

As shown in FIG. 18A, FIG. 18B and FIG. 18C, the level of glutathione in ovarian, pancreatic and TNBC cancer cells, respectively, decreased upon treatment of these cells with APC1.

Without wishing to be bound by theory these results may explain at least one pathway by which APC1 is acting to increase sensitivity of cancer cells to treatment with various agents, namely it appears that APC1 is acting to lower the cellular level of glutathione, thereby reducing the level of drug resistance in the cell.

The invention claimed is:

1. A method for treatment of triple negative breast cancer (TNBC) in a patient in need thereof, said method comprising administering to said patient an isolated polypeptide consisting of the amino acid sequence denoted by SEQ ID NO: 1 and an anti-cancer agent drug selected from the group consisting of doxorubicin and cisplatin.

2. A method for treatment of triple negative breast cancer (TNBC) in a patient in need thereof, said method comprising administering to said patient an isolated polypeptide consisting of the amino acid sequence denoted by SEQ ID NO: 1 and doxorubicin.

3. A method for treatment of triple negative breast cancer (TNBC) in a patient in need thereof, said method comprising administering to said patient an isolated polypeptide consisting of the amino acid sequence denoted by SEQ ID NO: 1 and cisplatin.

4. A method for treatment of ovarian cancer in a patient in need thereof, said method comprising administering to said patient an isolated polypeptide comprising the amino acid sequence denoted by SEQ ID NO: 1 and an anti-cancer drug selected from the group consisting of doxorubicin and cisplatin.

* * * * *